(12) United States Patent
Matsunaga et al.

(10) Patent No.: US 9,765,032 B2
(45) Date of Patent: Sep. 19, 2017

(54) METHOD FOR PRODUCING (R)-1,1,3-TRIMETHYL-4-AMINOINDANE

(71) Applicant: SUMITOMO CHEMICAL COMPANY, LIMITED, Tokyo (JP)

(72) Inventors: Tadafumi Matsunaga, Oita (JP); Natsuru Hiraguri, Oita (JP); Tomoaki Takahashi, Oita (JP); Tomohiko Inui, Osaka (JP); Masaya Tanimoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/117,058

(22) PCT Filed: Dec. 26, 2014

(86) PCT No.: PCT/JP2014/084766
§ 371 (c)(1),
(2) Date: Aug. 5, 2016

(87) PCT Pub. No.: WO2015/118793
PCT Pub. Date: Aug. 13, 2015

(65) Prior Publication Data
US 2017/0166532 A1     Jun. 15, 2017

(30) Foreign Application Priority Data

Feb. 7, 2014 (JP) ................. 2014-021976

(51) Int. Cl.
| | |
|---|---|
| C07D 231/10 | (2006.01) |
| C07D 231/12 | (2006.01) |
| C07D 231/16 | (2006.01) |
| C07C 209/88 | (2006.01) |
| C07C 211/60 | (2006.01) |
| C07B 57/00 | (2006.01) |

(52) U.S. Cl.
CPC ............ *C07D 231/10* (2013.01); *C07B 57/00* (2013.01); *C07C 209/88* (2013.01); *C07C 211/60* (2013.01); *C07D 231/12* (2013.01); *C07D 231/16* (2013.01)

(58) Field of Classification Search
None
See application file for complete search history.

(56) References Cited

U.S. PATENT DOCUMENTS

| | | | |
|---|---|---|---|
| 5,093,347 A | 3/1992 | Graneto et al. | |
| 5,728,869 A | 3/1998 | Briner | |
| 8,580,836 B2 | 11/2013 | Matsuzaki et al. | |
| 9,227,911 B2 * | 1/2016 | Ujita | C07C 51/412 |
| 9,284,260 B2 | 3/2016 | Takahashi et al. | |
| 2015/0181876 A1 | 7/2015 | Matsuzaki | |
| 2015/0344431 A1 | 12/2015 | Matsunaga | |

FOREIGN PATENT DOCUMENTS

| | | |
|---|---|---|
| CN | 102958367 A | 3/2013 |
| JP | 10-72410 A | 3/1998 |
| JP | 2012-25735 A | 2/2012 |
| WO | WO 2011/162397 A1 | 12/2011 |
| WO | WO 2014/013842 A1 | 1/2014 |
| WO | WO 2014/034957 A1 | 3/2014 |
| WO | WO 2014/069611 A1 | 5/2014 |
| WO | WO 2014/103812 A1 | 7/2014 |

OTHER PUBLICATIONS

Burwell et al., "The Action of Some Strong Acids on Secondary Phenylpentanes," JACS, vol. 77, May 20, 1955, pp. 2766-2771.
Cliffe et al., "The Acid-catalysed Rearrangement of Tetrahydroquinoline Derivatives," J. Chem. Soc., 1966, pp. 514-517.
Eliel et al., "Racemization of Phenylalkanes in Prescence of lewis Acids," The Journal of Organic Chemistry, vol. 22, No. 3, Apr. 29, 1957, pp. 231-324.
International Report on Patentability and Written Opinion of the International Searching Authority (Forms PCT/IB/373 and PCT/ISA/237) dated Aug. 9, 2016, for International Application No. PCT/JP2014/084766.
International Search Report (Form PCT/ISA/210) dated Mar. 31, 2015, for International Application No. PCT/JP2014/084766.
Chinese Office Action and Search Report dated May 24, 2017 for Application No. 201480075004.4 along with an English translation thereof.
Extended European Search Report dated Jun. 2, 2017 for Application No. 14882034.3.

* cited by examiner

*Primary Examiner* — Kamal Saeed
(74) *Attorney, Agent, or Firm* — Birch, Stewart, Kolasch & Birch, LLP

(57) ABSTRACT

A method for producing (R)-1,1,3-trimethyl-4-aminoindane includes the following steps (A), (B), and (C). Step (A) is a step of optically resolving 1,1,3-trimethyl-4-aminoindane to obtain (R)-1,1,3-trimethyl-4-aminoindane and (S)-1,1,3-trimethyl-4-aminoindane, step (B) is a step of racemizing the (S)-1,1,3-trimethyl-4-aminoindane obtained in the step (A) or (C) to obtain 1,1,3-trimethyl-4-aminoindane, and step (C) is a step of optically resolving the 1,1,3-trimethyl-4-aminoindane obtained in the step (B) to obtain (R)-1,1,3-trimethyl-4-aminoindane and (S)-1,1,3-trimethyl-4-aminoindane.

13 Claims, 19 Drawing Sheets

[Fig. 1]
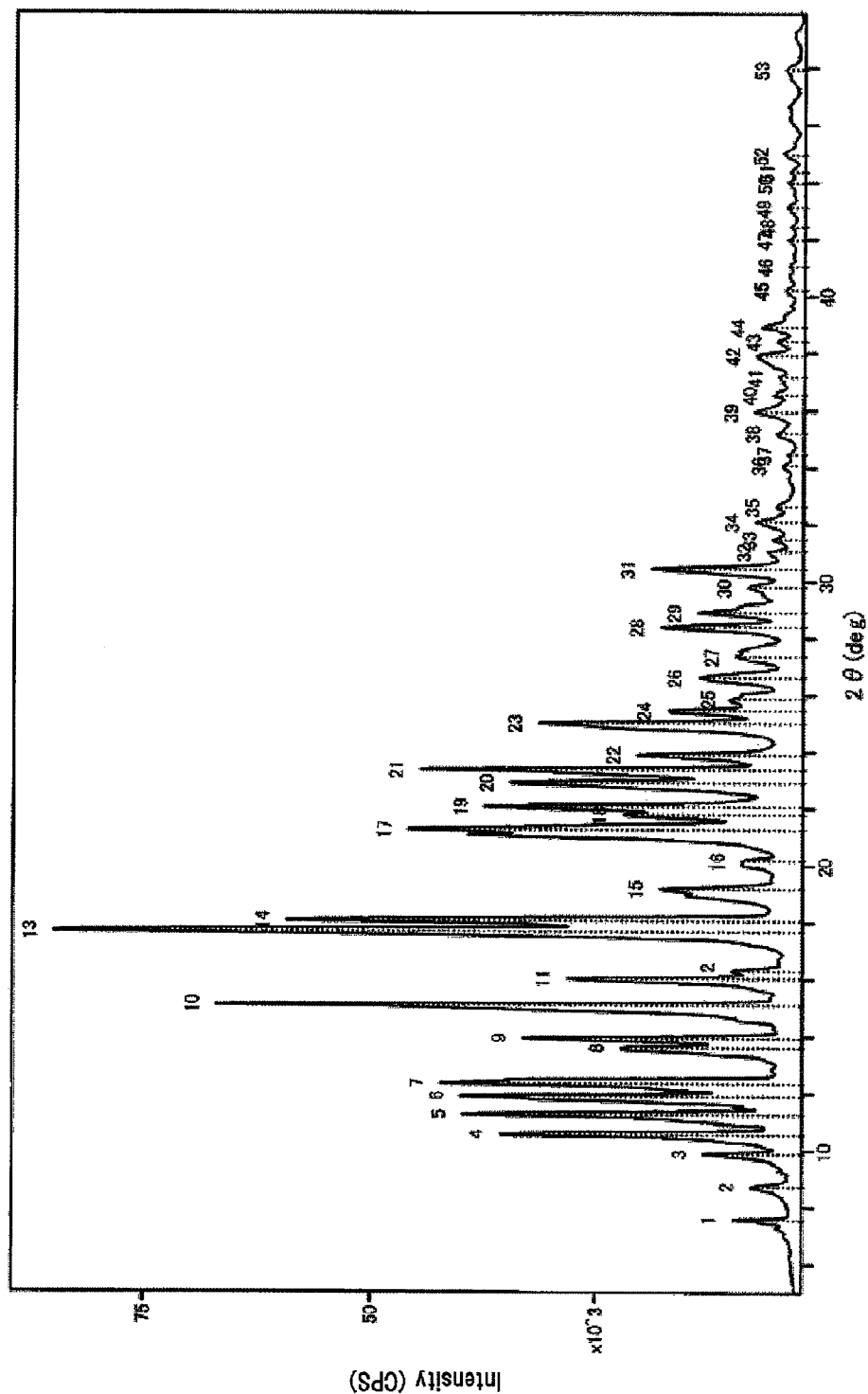

[Fig. 2]
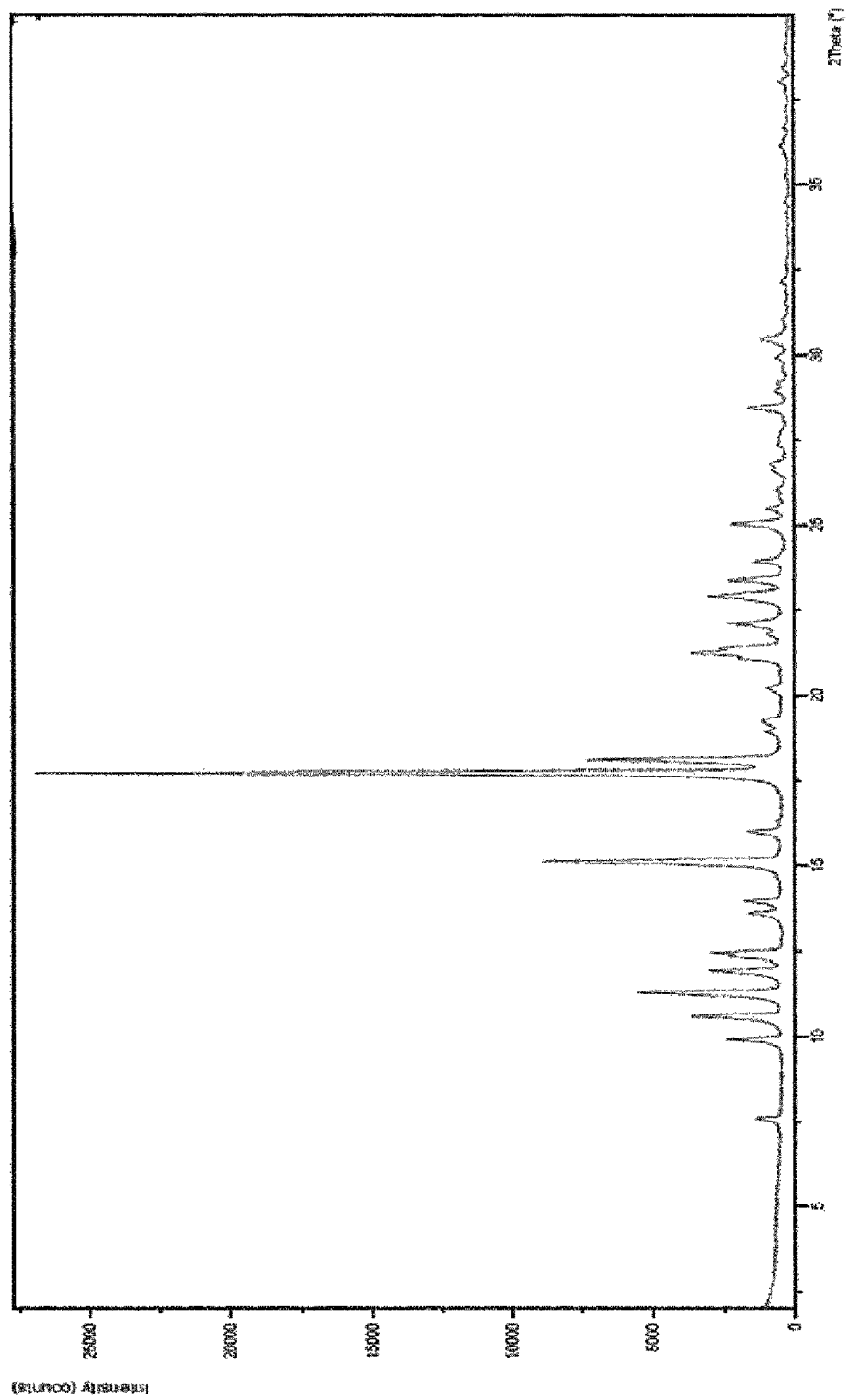

[Fig. 3]
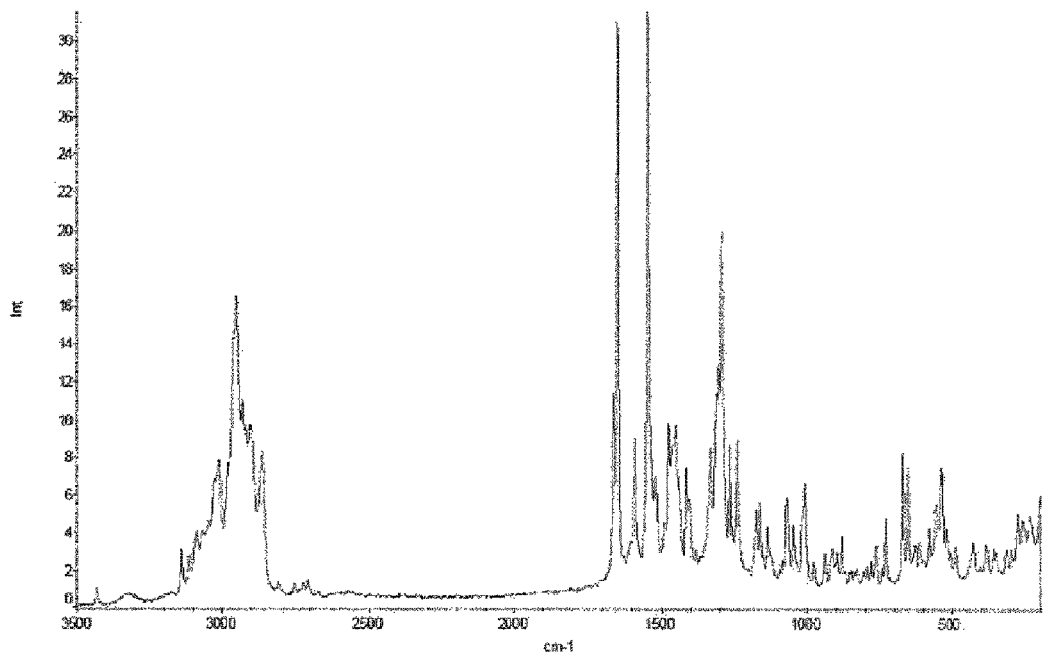
[Fig. 4]
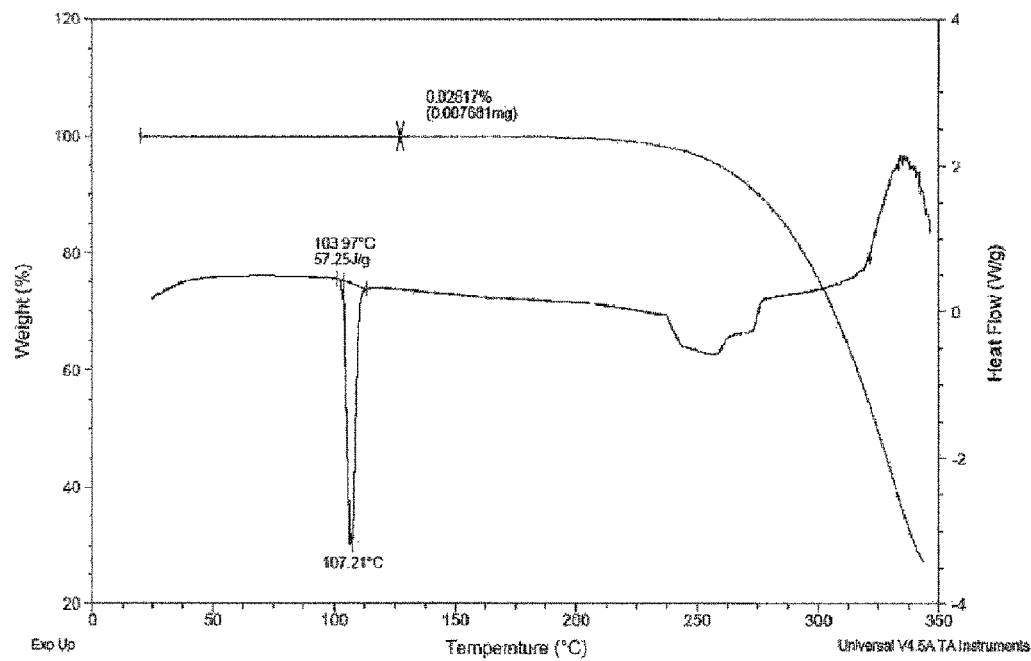

[Fig. 5]
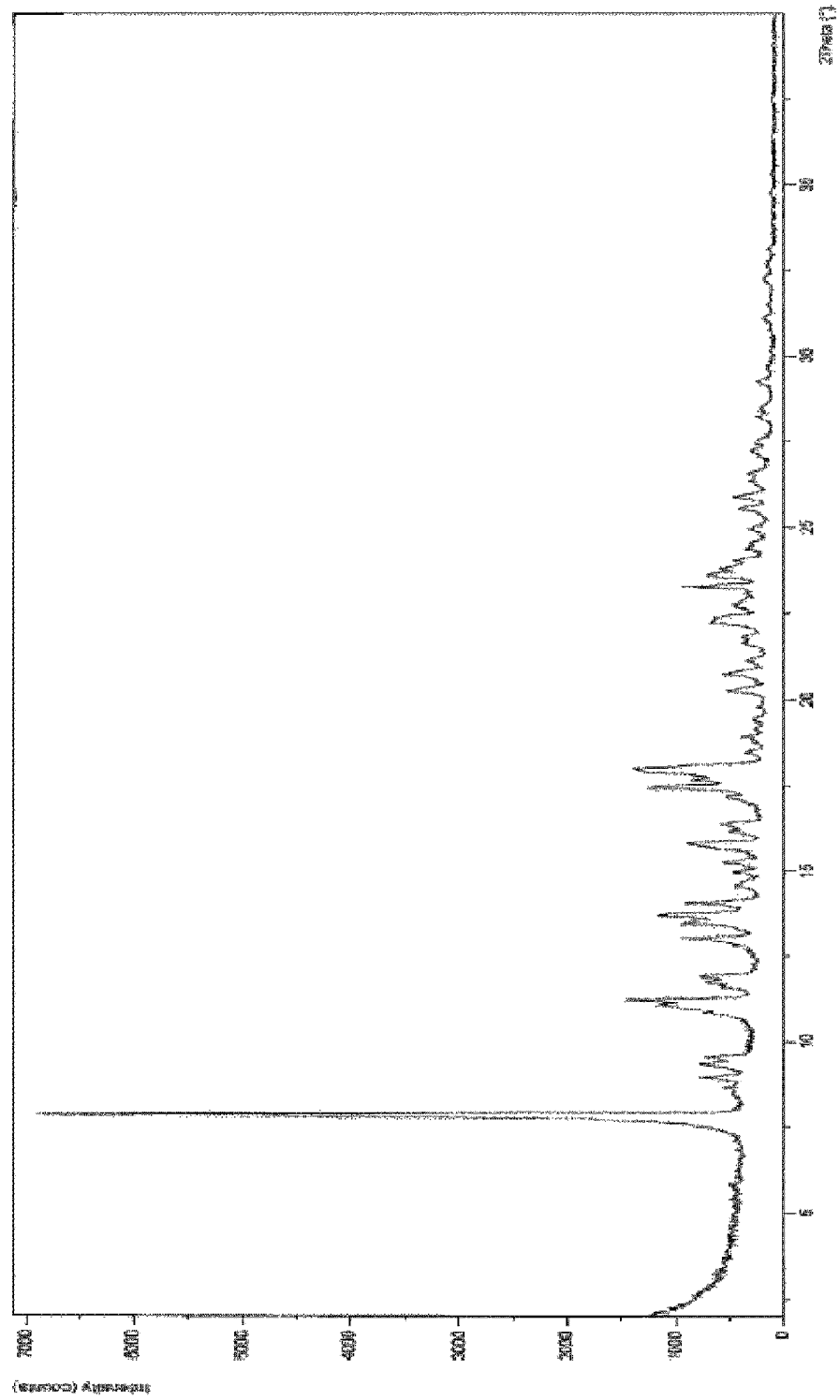

[Fig. 6]
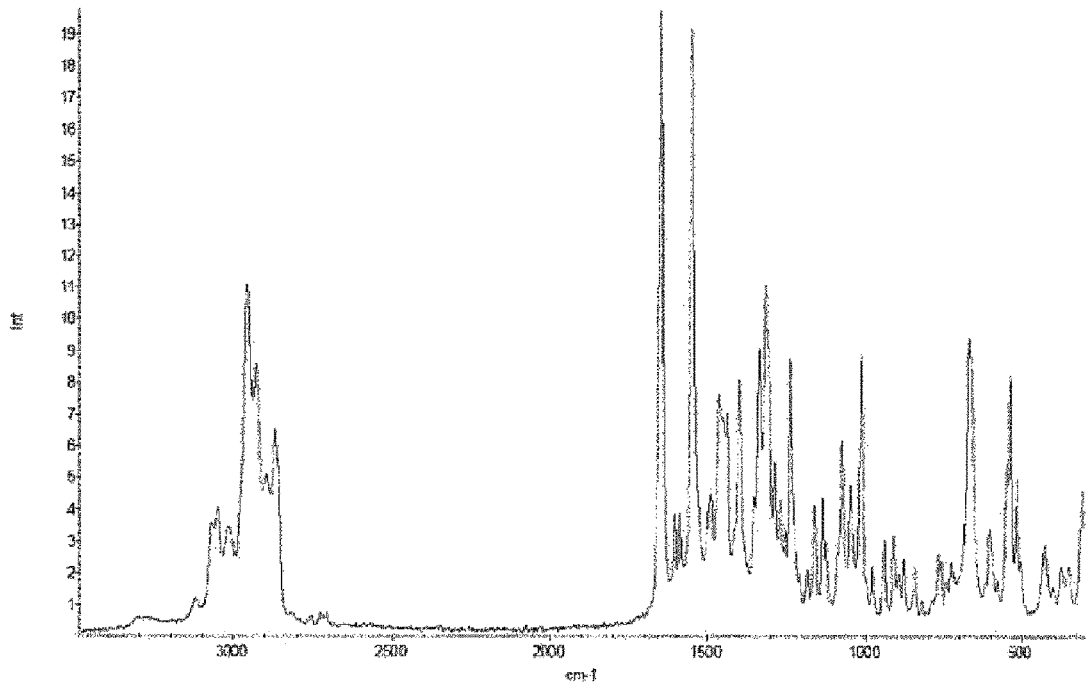
[Fig. 7]
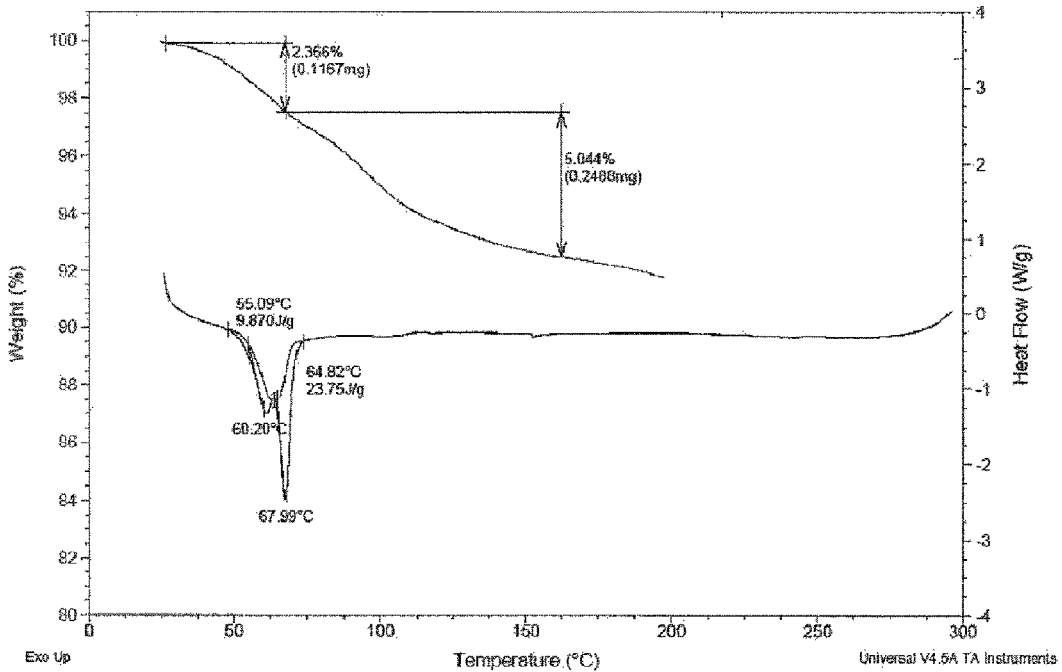

[Fig. 8]
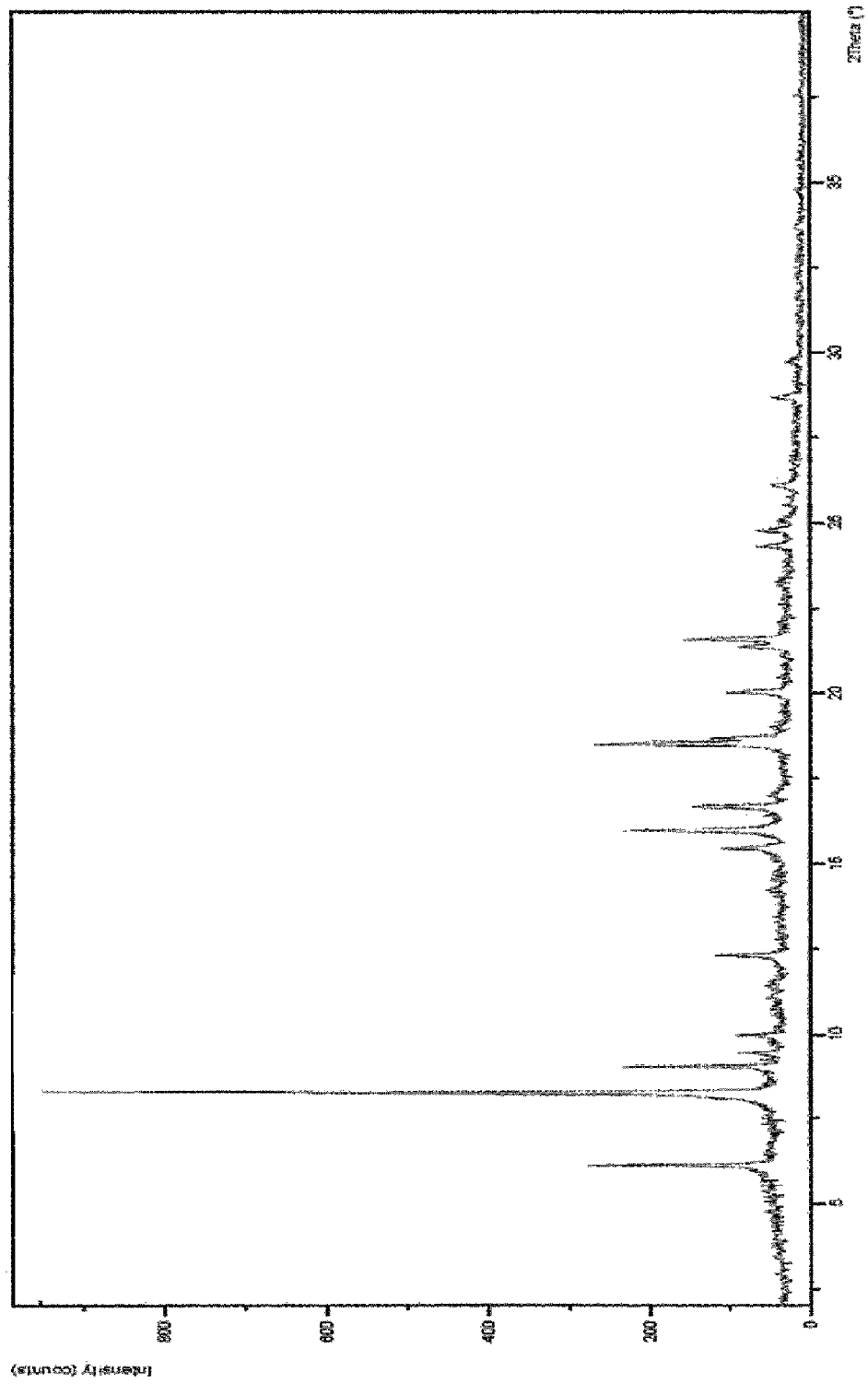

[Fig. 9]
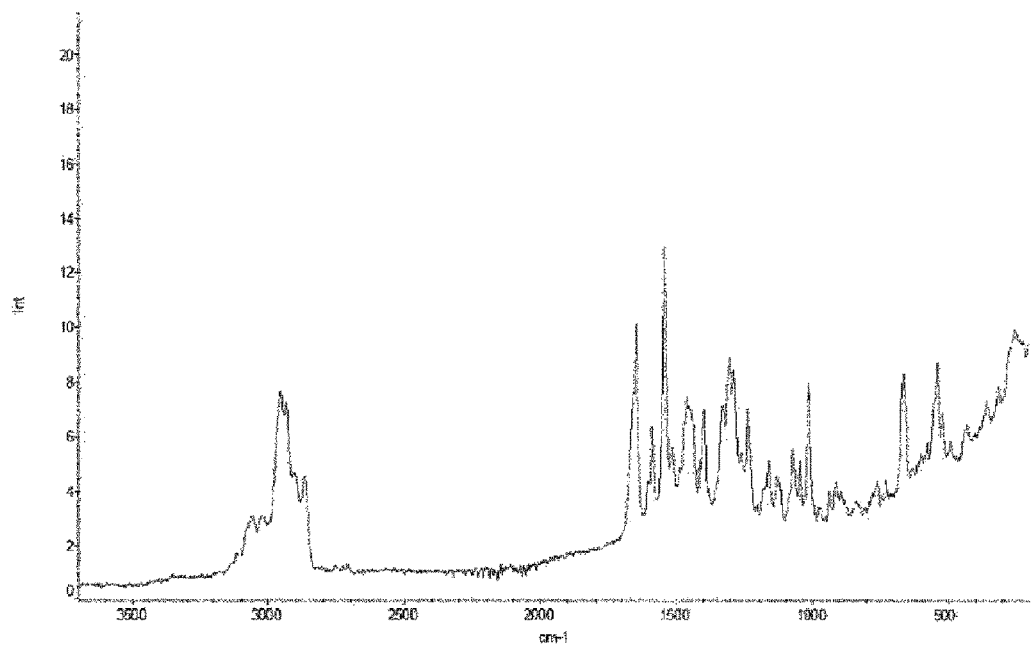
[Fig. 10]
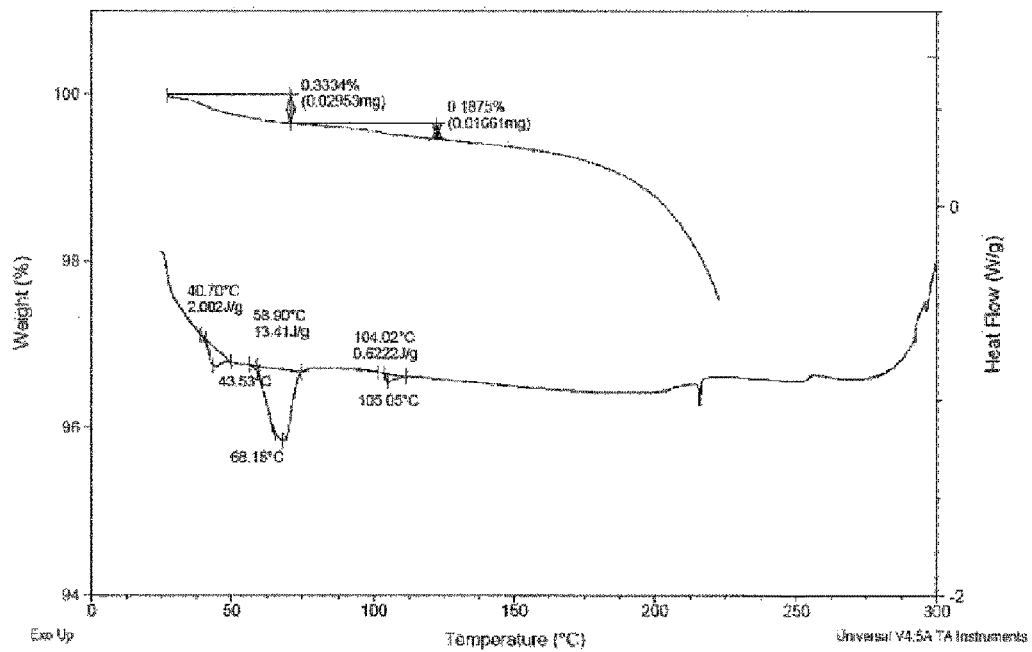

[Fig. 11]
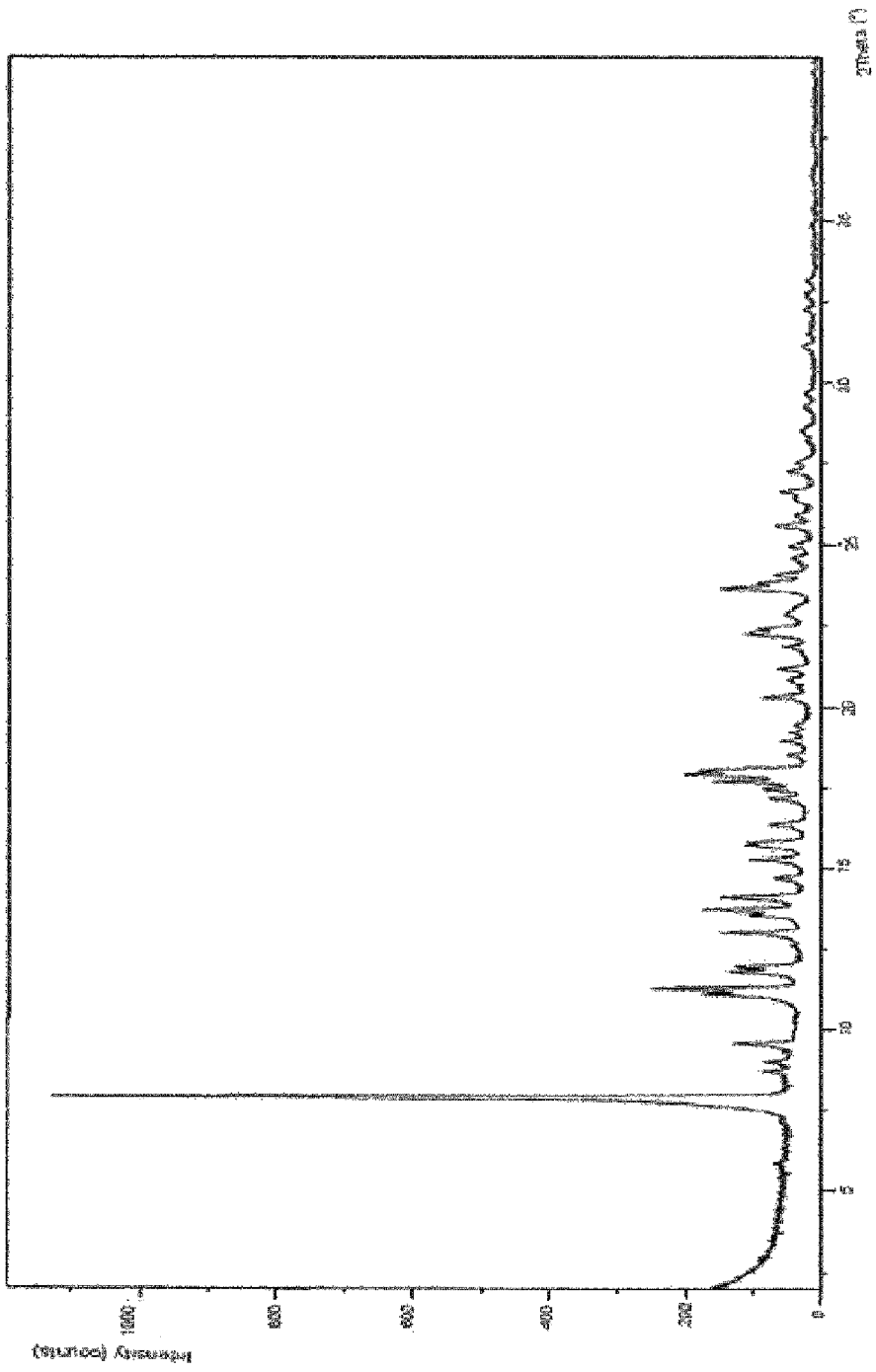

[Fig. 12]
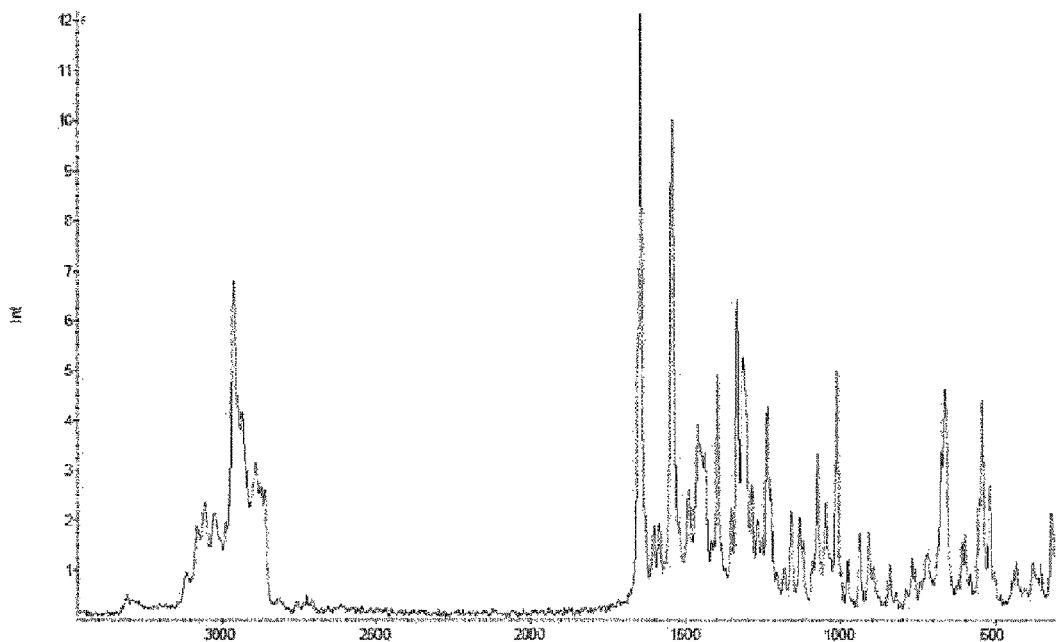
[Fig. 13]
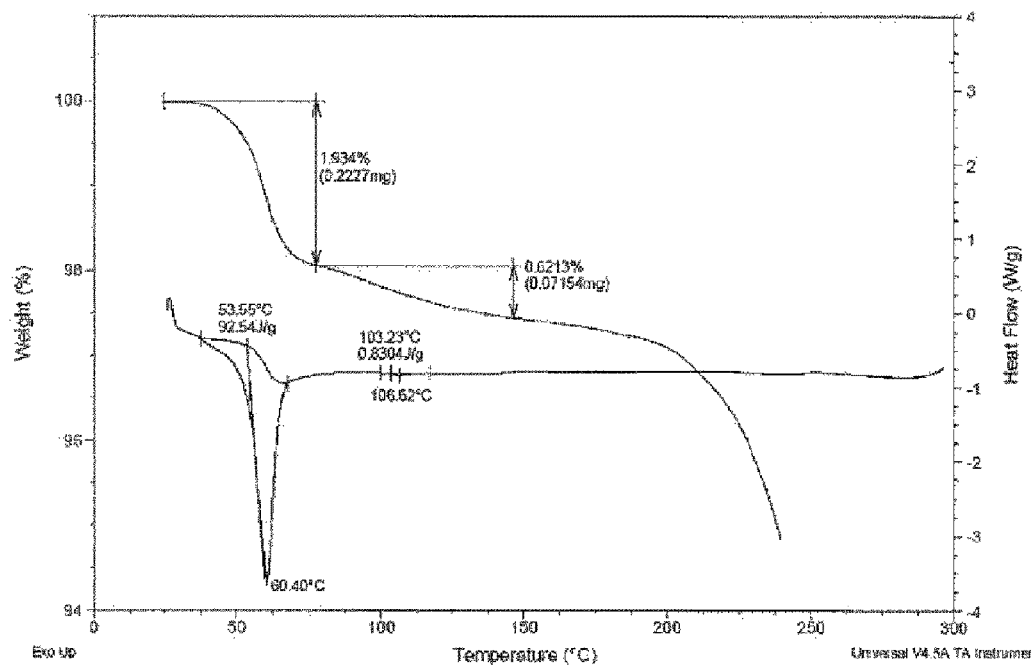

[Fig. 14]
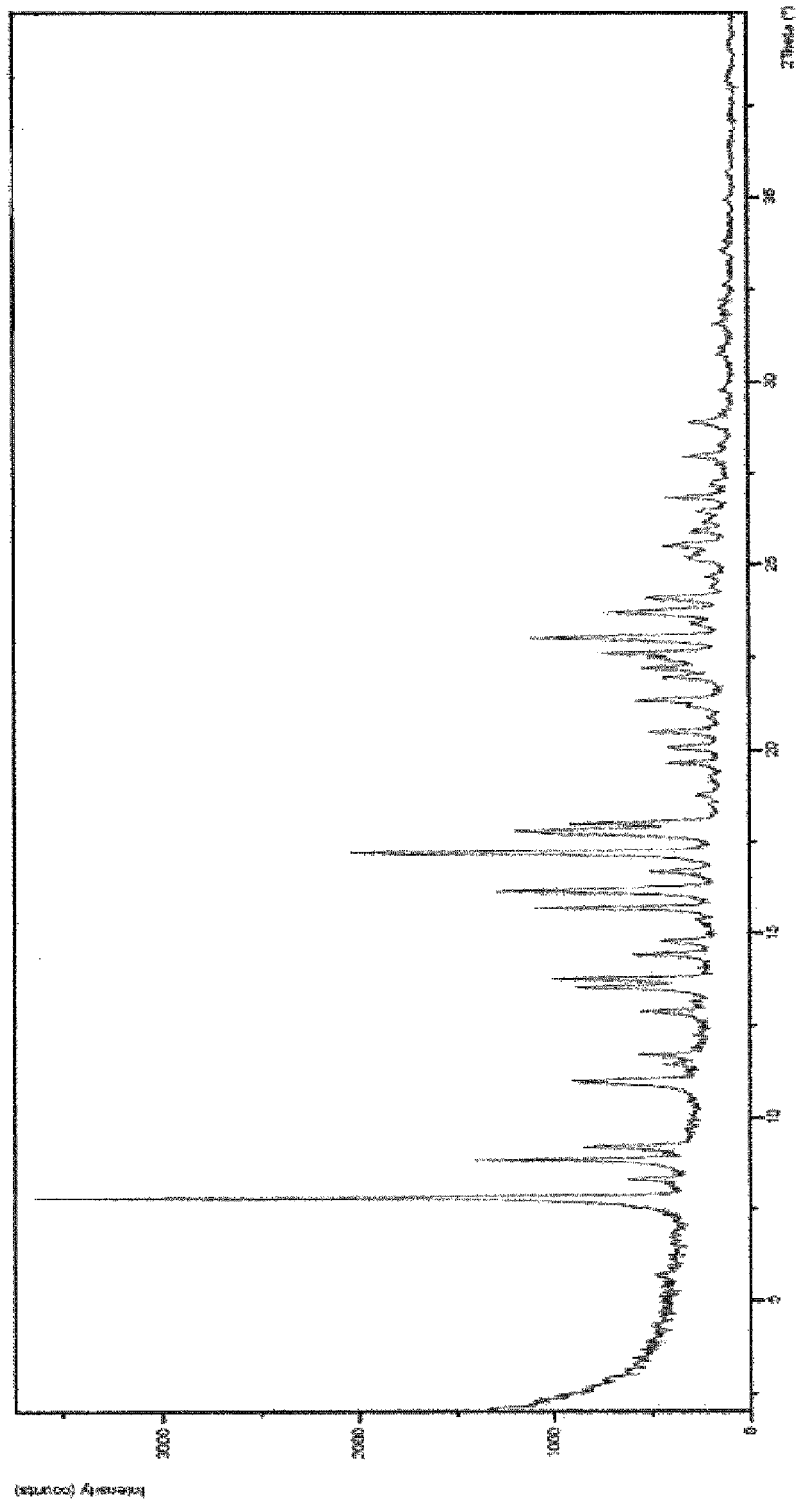

[Fig. 15]
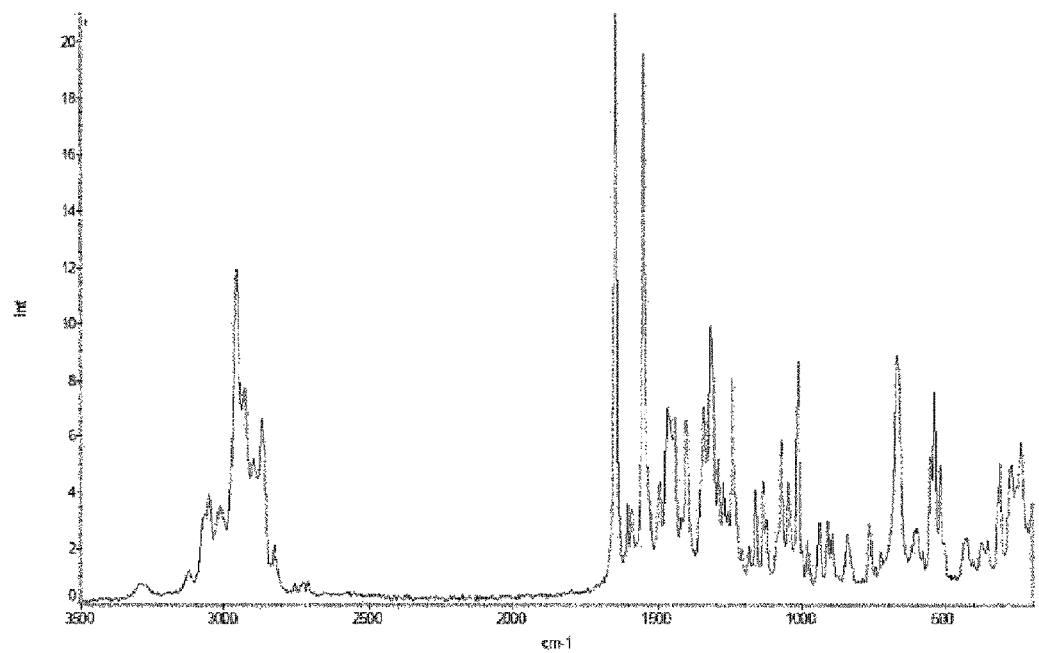
[Fig. 16]
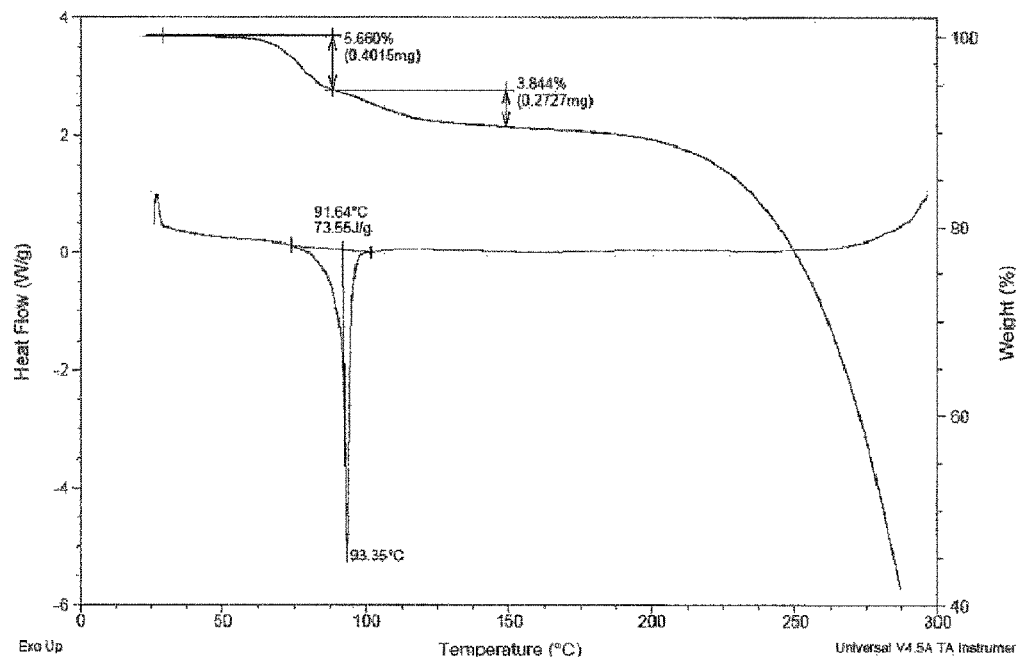

[Fig. 17]
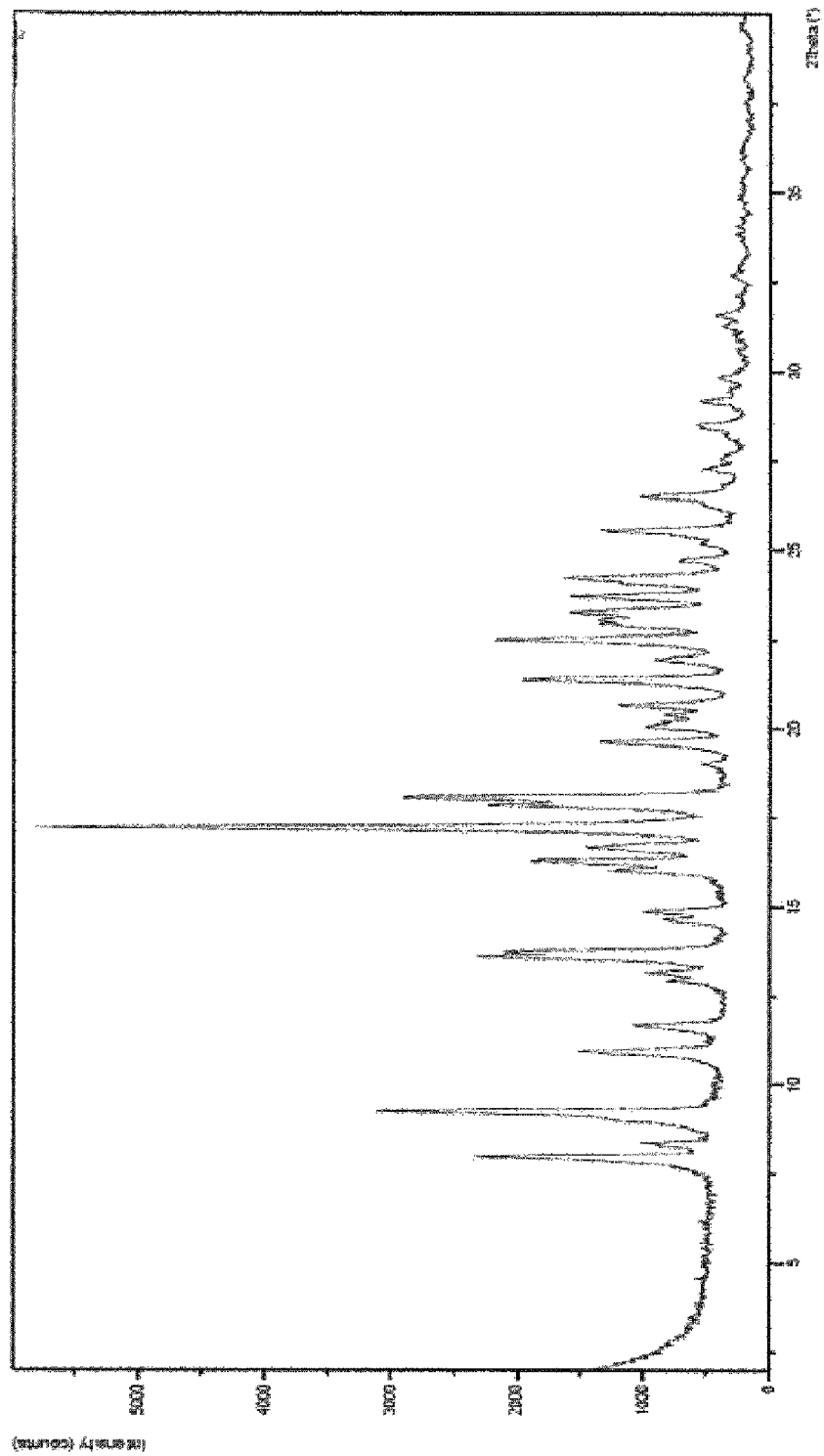

[Fig. 18]
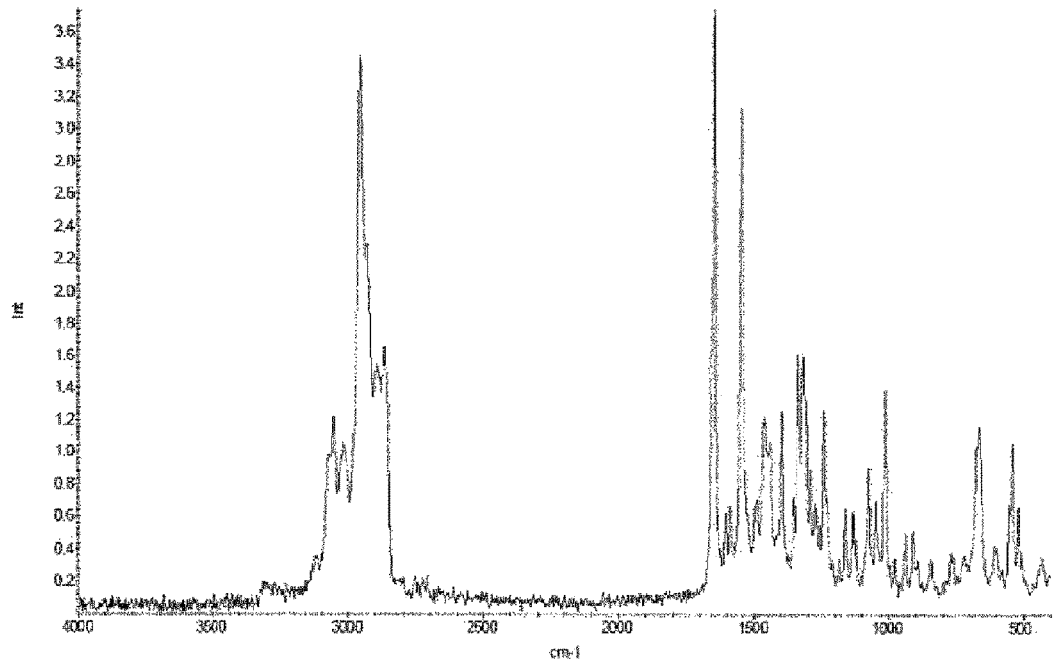
[Fig. 19]
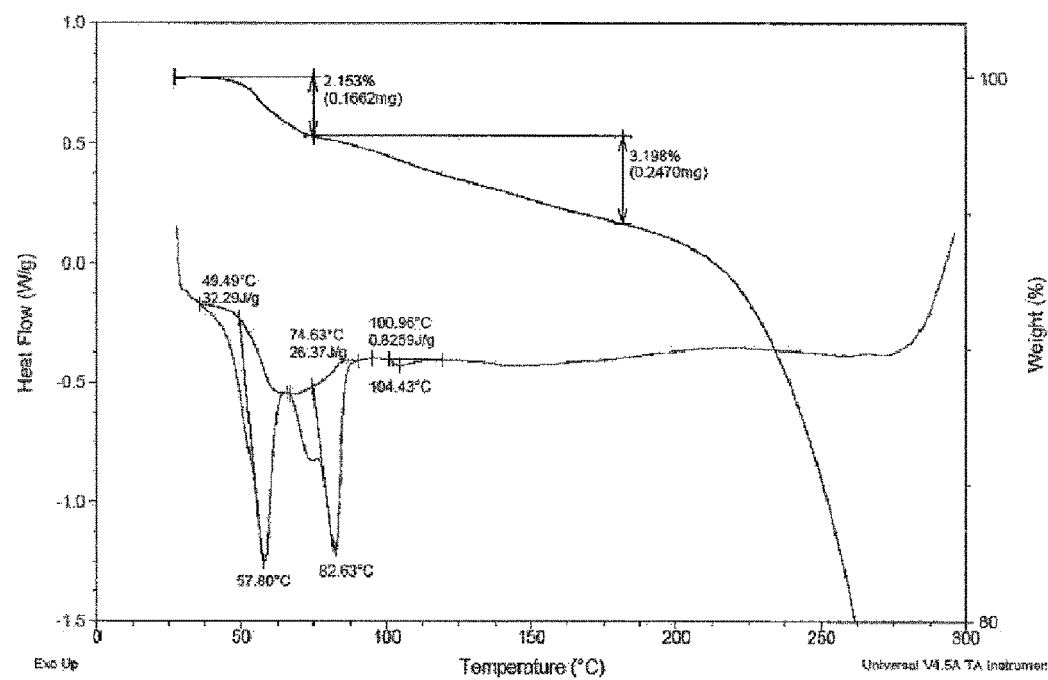

[Fig. 20]
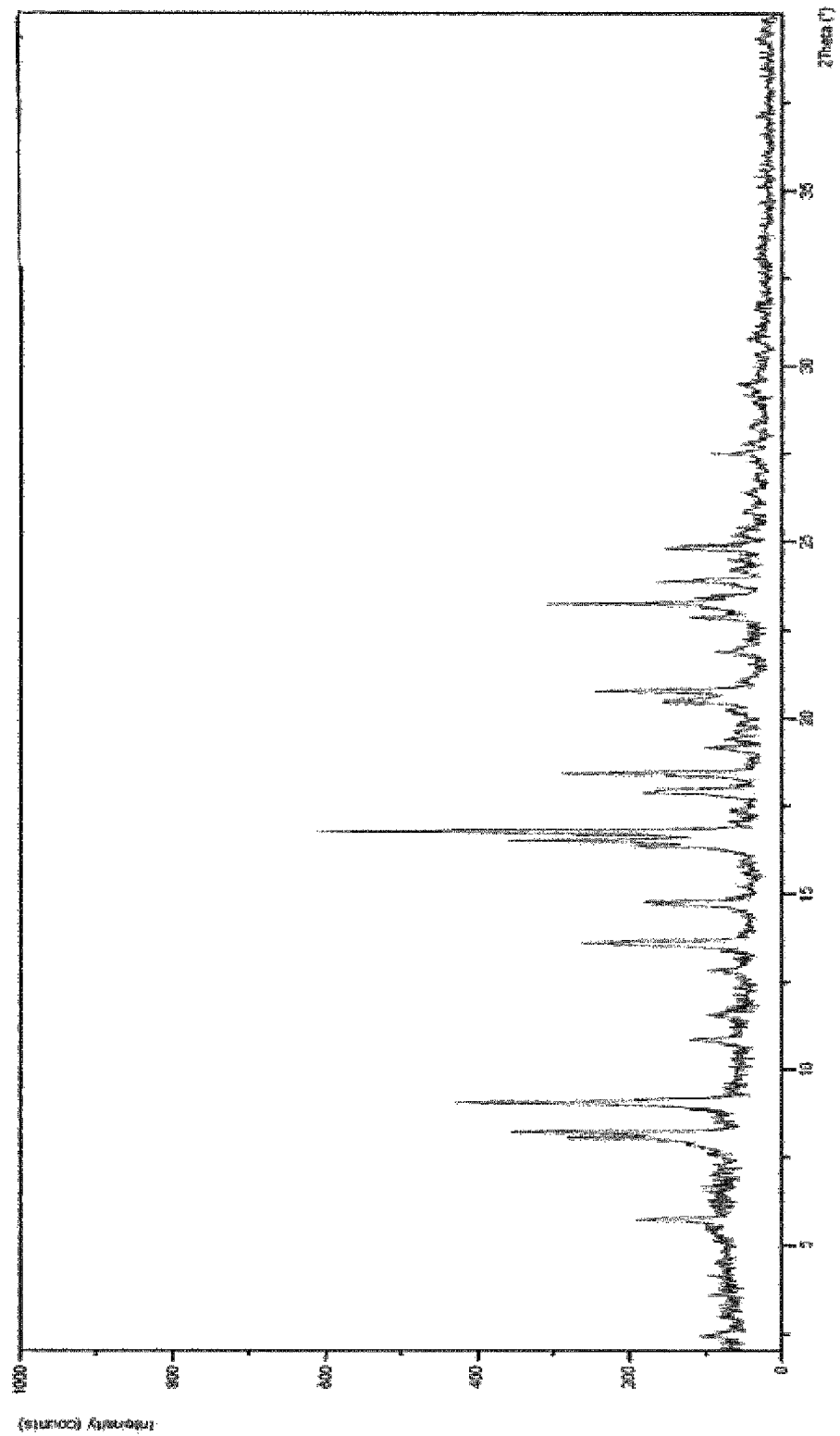

[Fig. 21]
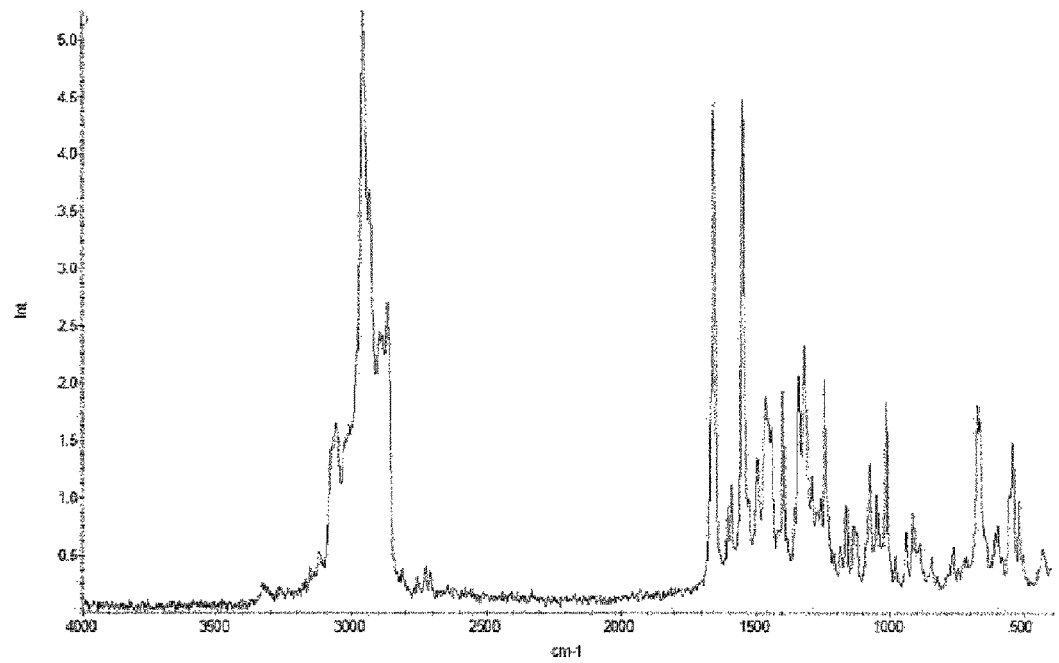
[Fig. 22]
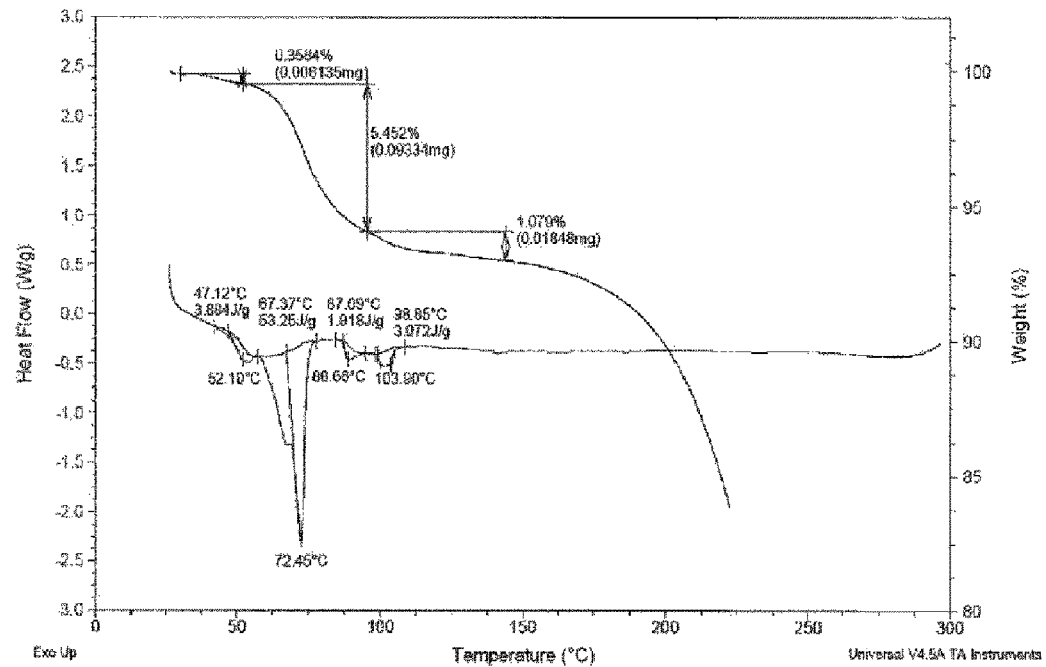

[Fig. 23]
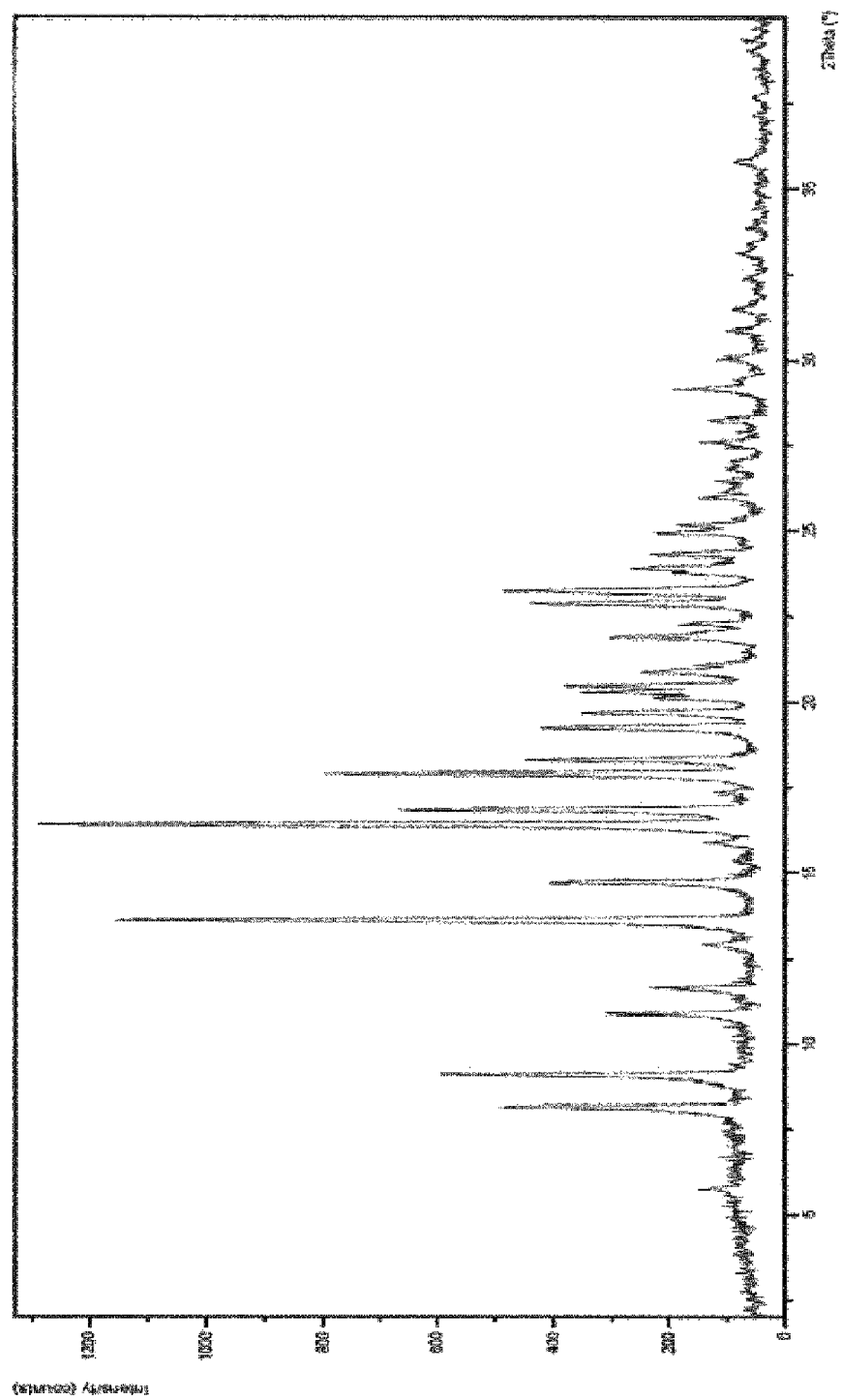

[Fig. 24]
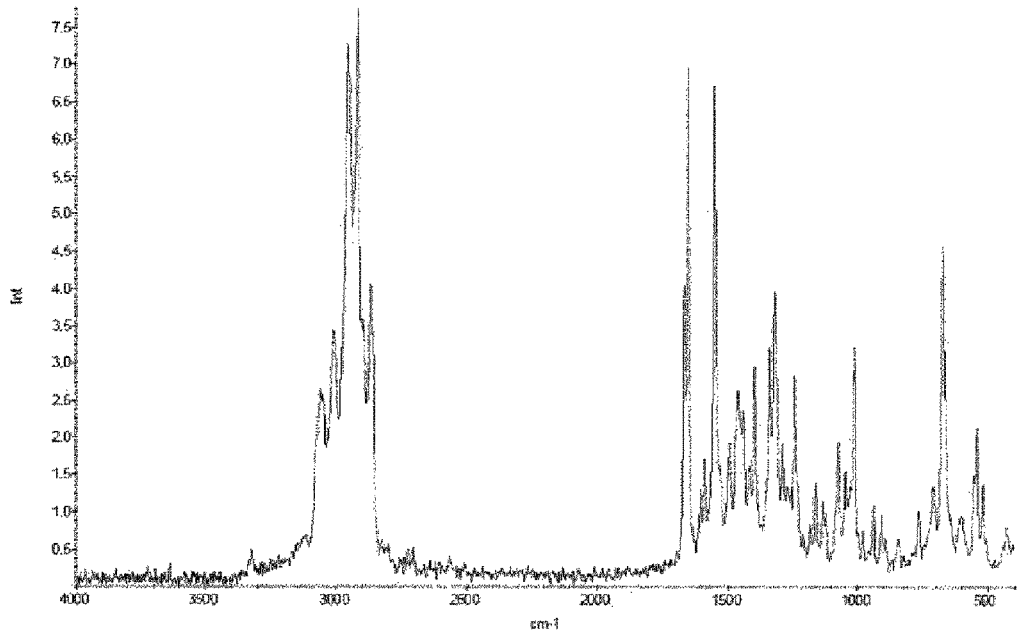
[Fig. 25]
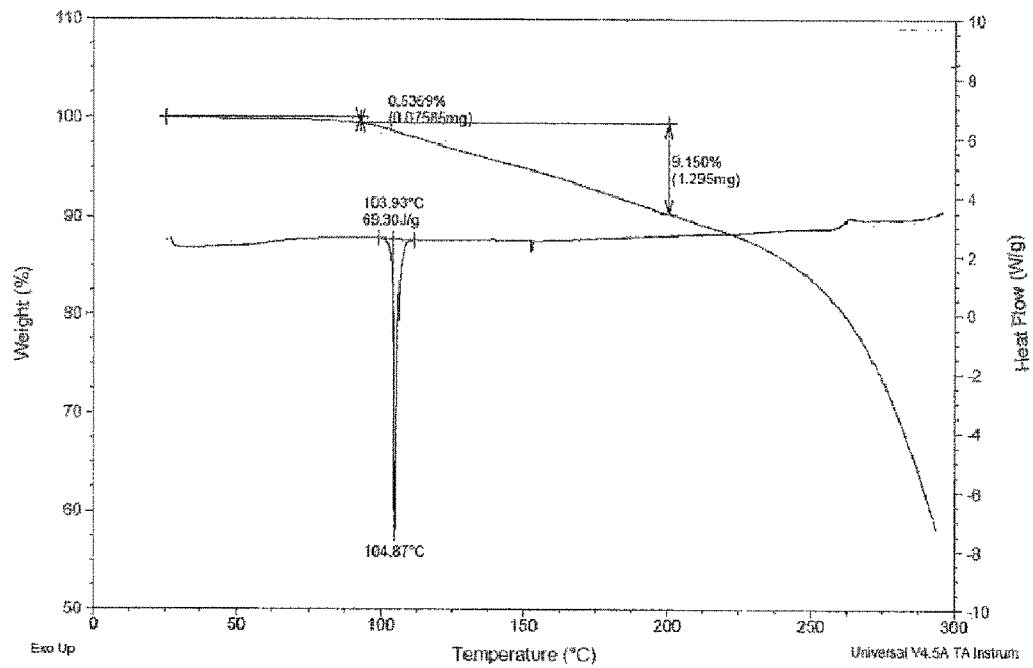

[Fig. 26]
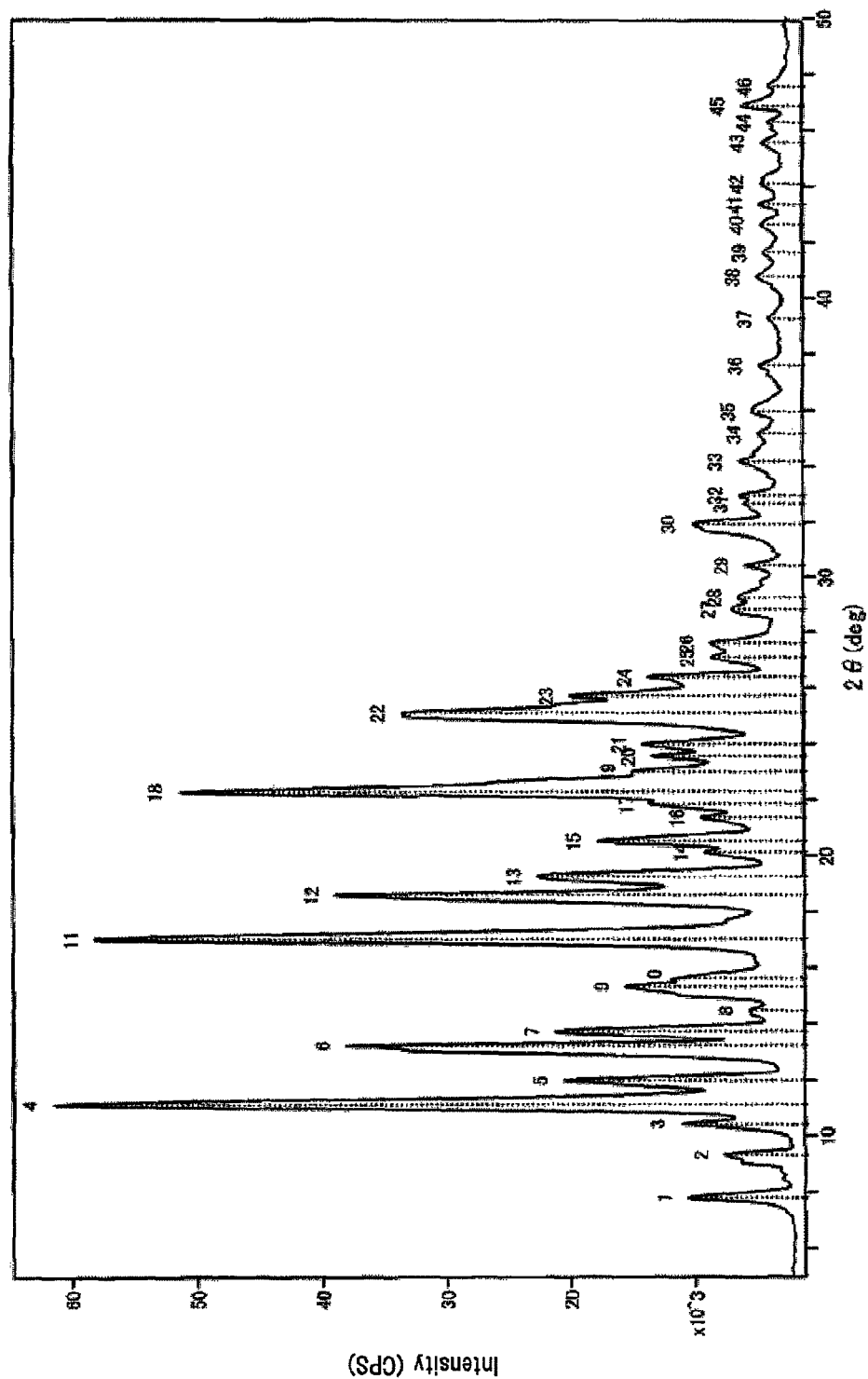

[Fig. 27]
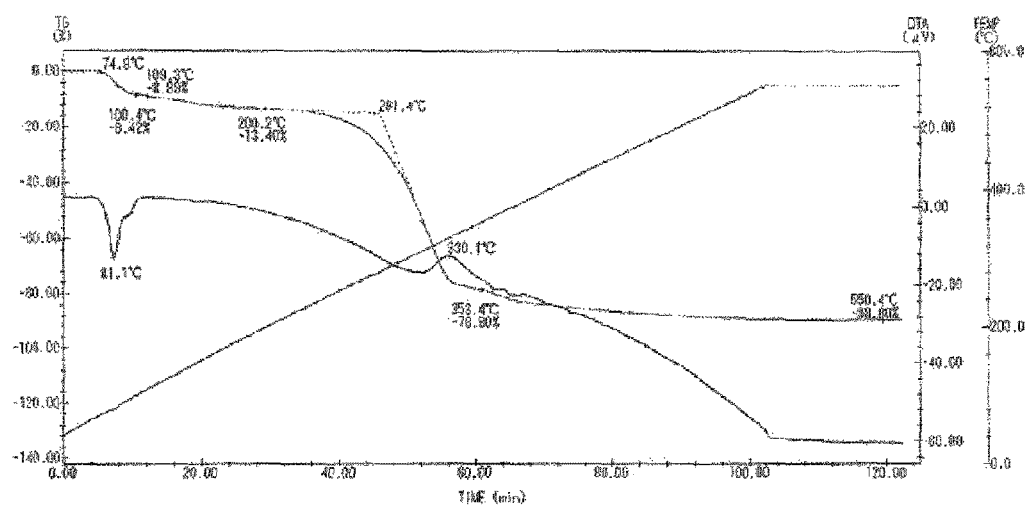

METHOD FOR PRODUCING (R)-1,1,3-TRIMETHYL-4-AMINOINDANE

TECHNICAL FIELD

The present invention relates to a method for producing (R)-1,1,3-trimethyl-4-aminoindane.

BACKGROUND ART

Patent Document 1 describes that (R)-1,1,3-trimethyl-4-aminoindane is useful as an intermediate for the synthesis of (R)-(−)-N-(1,1,3-trimethylindan-4-yl)-1-methyl-3-difluoromethylpyrazole-4-carboxylic acid amide having a plant disease controlling effect.

PRIOR ART DOCUMENT

Patent Document

Patent Document 1: WO2011/162397

SUMMARY OF INVENTION

Problems to be Solved by the Invention

There has been a demand for a method for producing (R)-1,1,3-trimethyl-4-aminoindane in a high yield.

Means for Solving Problems

The present invention includes the following aspects of the inventions.

[1] A method for producing (R)-1,1,3-trimethyl-4-aminoindane, including the following steps (A), (B), and (C):

(A): a step of optically resolving 1,1,3-trimethyl-4-aminoindane to obtain (R)-1,1,3-trimethyl-4-aminoindane and (S)-1,1,3-trimethyl-4-aminoindane;

(B): a step of racemizing the (S)-1,1,3-trimethyl-4-aminoindane obtained in the step (A) or (C) to obtain 1,1,3-trimethyl-4-aminoindane; and (C): a step of optically resolving the 1,1,3-trimethyl-4-aminoindane obtained in the step (B) to obtain (R)-1,1,3-trimethyl-4-aminoindane and (S)-1,1,3-trimethyl-4-aminoindane.

[2] The production method as described in [1], in which the steps (B) and (C) are repeated.

[3] The production method as described in [1] or [2], in which the step (C) is a step of optically resolving the 1,1,3-trimethyl-4-aminoindane obtained in the step (B) and the 1,1,3-trimethyl-4-aminoindane obtained in a step other than the step (B) to obtain (R)-1,1,3-trimethyl-4-aminoindane.

[4] The production method as described in [1], including the following steps (A), (B'), (D), and (E):

(A): a step of optically resolving 1,1,3-trimethyl-4-aminoindane to obtain (R)-1,1,3-trimethyl-4-aminoindane and (S)-1,1,3-trimethyl-4-aminoindane;

(B'): a step of racemizing the (S)-1,1,3-trimethyl-4-aminoindane obtained in the step (A) or (E) to obtain 1,1,3-trimethyl-4-aminoindane;

(D): a step of purifying the 1,1,3-trimethyl-4-aminoindane obtained in the step (B'); and (E): a step of optically resolving the 1,1,3-trimethyl-4-aminoindane obtained in the step (D) to obtain (R)-1,1,3-trimethyl-4-aminoindane and (S)-1,1,3-trimethyl-4-aminoindane.

[5] The production method as described in [4], in which the steps (B'), (D), and (E) are repeated.

[6] The production method as described in any one of [1] to [5], in which the step (B) or (B') is a step of bringing the (S)-1,1,3-trimethyl-4-aminoindane obtained in the step (A) into contact with a transition metal catalyst to perform racemization.

[7] The production method as described in any one of [1] to [6], in which the step (A) is a step including the following steps (A1), (A2), (A3), and (A4):

(A1): a step of mixing 1,1,3-trimethyl-4-aminoindane with D-tartaric acid and methanol to obtain a mixture including a methanol solvate of D-tartrate of (R)-1,1,3-trimethyl-4-aminoindane and D-tartrate of (S)-1,1,3-trimethyl-4-aminoindane;

(A2): a step of separating a solution containing D-tartrate of (S)-1,1,3-trimethyl-4-aminoindane and the methanol solvate of D-tartrate of (R)-1,1,3-trimethyl-4-aminoindane from the mixture obtained in the step (A1);

(A3): a step of mixing the methanol solvate of D-tartrate of (R)-1,1,3-trimethyl-4-aminoindane obtained in the step (A2) and an aqueous alkali metal hydroxide solution or aqueous alkali metal carbonate solution to obtain (R)-1,1,3-trimethyl-4-aminoindane; and (A4): a step of mixing the solution including the D-tartrate of (S)-1,1,3-trimethyl-4-aminoindan obtained in the step (A2) and an aqueous alkali metal hydroxide solution or aqueous alkali metal carbonate solution to obtain (S)-1,1,3-trimethyl-4-aminoindane.

[8] The production method as described in [7], in which water is mixed into the reaction system prior to the step (A2).

[9] The production method as described in any one of [4] to [8], in which the step (D) is a step including the following steps (D1), (D2), (D3), and (D4):

(D1): a step of reacting the 1,1,3-trimethyl-4-aminoindane obtained in the step (B') with hydrogen hydride in the presence of water and a water-insoluble organic solvent;

(D2): a step of separating a layer dissolving therein a hydrogen halide salt of 1,1,3-trimethyl-4-aminoindane included in the mixture obtained in the step (D1) from other layer;

(D3): a step of precipitating the hydrogen halide salt of 1,1,3-trimethyl-4-aminoindane from the layer dissolving therein the hydrogen halide salt of 1,1,3-trimethyl-4-aminoindane obtained in the step (D2); and (D4): a step of withdrawing the hydrogen halide salt of 1,1,3-trimethyl-4-aminoindane obtained in the step (D3) and reacting thus obtained hydrogen halide salt with a base.

[10] The production method as described in [9], in which the hydrogen halide is hydrogen chloride.

[11] A method for producing a compound represented by the following formula (1):

(1)

wherein $R^1$ and $R^2$ each independently represent an alkyl group which may be substituted with a halogen atom, or a hydrogen atom), including the following steps (A), (B), (C), and (F):

(A): a step of optically resolving 1,1,3-trimethyl-4-aminoindane to obtain (R)-1,1,3-trimethyl-4-aminoindane and (S)-1,1,3-trimethyl-4-aminoindane;

(B): a step of racemizing the (S)-1,1,3-trimethyl-4-aminoindane obtained in the step (A) or (C) to obtain 1,1,3-trimethyl-4-aminoindane;

(C): a step of optically resolving the 1,1,3-trimethyl-4-aminoindane obtained in the step (B) to obtain (R)-1,1,3-trimethyl-4-aminoindane and (S)-1,1,3-trimethyl-4-aminoindane; and (F): a step of reacting the (R)-1,1,3-trimethyl-4-aminoindane obtained in the step (C) with a compound represented by the formula (2) to obtain a compound represented by the formula (1):

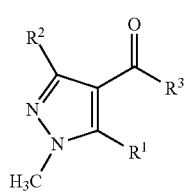

(2)

wherein $R^1$ and $R^2$ represent the same meanings as above, and $R^3$ represents a halogen atom, a hydroxyl group, or an alkoxy group which may be substituted with a halogen atom.

[12] A method for producing a compound represented by the following formula (1):

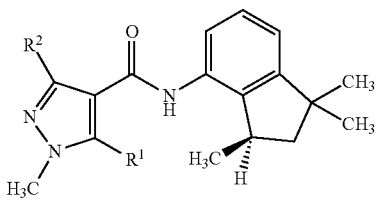

(1)

wherein $R^1$ and $R^2$ each independently represent an alkyl group which may be substituted with a halogen atom, or a hydrogen atom, including the following steps (A), (B), (C), (G), and (H):

(A): a step of optically resolving 1,1,3-trimethyl-4-aminoindane to obtain (R)-1,1,3-trimethyl-4-aminoindane and (S)-1,1,3-trimethyl-4-aminoindane;

(B): a step of racemizing the (S)-1,1,3-trimethyl-4-aminoindane obtained in the step (A) or (C) to obtain 1,1,3-trimethyl-4-aminoindane;

(C): a step of optically resolving the 1,1,3-trimethyl-4-aminoindane obtained in the step (B) to obtain (R)-1,1,3-trimethyl-4-aminoindane and (S)-1,1,3-trimethyl-4-aminoindane;

(G): a step of obtaining a compound represented by the formula (4) from a compound represented by the formula (3):

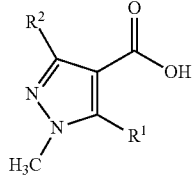

(3)

(in the formula, $R^1$ and $R^2$ represent the same meanings as above)

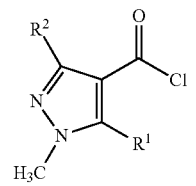

(4)

(in the formula, $R^1$ and $R^2$ represent the same meanings as above); and (H): a step of reacting the compound represented by the formula (4) obtained in the step (G) with the (R)-1,1,3-trimethyl-4-aminoindane obtained in the step (C) in the presence of a base to obtain the compound represented by the formula (1).

[13] The production method as described in [11] or [12], in which $R^1$ is a hydrogen atom or a methyl group, and $R^2$ is a methyl group, a monofluoromethyl group, a difluoromethyl group, or a trifluoromethyl group.

Advantage Effects of Invention

According to the present invention, (R)-1,1,3-trimethyl-4-aminoindane can be obtained in a high yield.

BRIEF DESCRIPTION OF DRAWINGS

FIG. 1 shows an XRD chart of (R)-(−)-N-(1,1,3-trimethylindan-4-yl)-1-methyl-3-difluoromethylpyrazole-4-carboxylic acid amide in Example 3.

FIG. 2 shows an XRD chart of (R)-(−)-N-(1,1,3-trimethylindan-4-yl)-1-methyl-3-difluoromethylpyrazole-4-carboxylic acid amide in Reference Example 1.

FIG. 3 shows an FT-Raman spectrum of (R)-(−)-N-(1,1,3-trimethylindan-4-yl)-1-methyl-3-difluoromethylpyrazole-4-carboxylic acid amide in Reference Example 1.

FIG. 4 shows a DSC/TGA chart of (R)-(−)-N-(1,1,3-trimethylindan-4-yl)-1-methyl-3-difluoromethylpyrazole-4-carboxylic acid amide in Reference Example 1.

FIG. 5 shows an XRD chart of an ethanol/hydrate of (R)-(−)-N-(1,1,3-trimethylindan-4-yl)-1-methyl-3-difluoromethylpyrazole-4-carboxylic acid amide in Reference Example 2.

FIG. 6 shows an FT-Raman spectrum of an ethanol/hydrate of (R)-(−)-N-(1,1,3-trimethylindan-4-yl)-1-methyl-3-difluoromethylpyrazole-4-carboxylic acid amide in Reference Example 2.

FIG. 7 shows a DSC/TGA chart of an ethanol/hydrate of (R)-(−)-N-(1,1,3-trimethylindan-4-yl)-1-methyl-3-difluoromethylpyrazole-4-carboxylic acid amide in Reference Example 2.

FIG. 8 shows an XRD chart of (R)-(−)-N-(1,1,3-trimethylindan-4-yl)-1-methyl-3-difluoromethylpyrazole-4-carboxylic acid amide in Reference Example 4.

FIG. 9 shows an FT-Raman spectrum of (R)-(−)-N-(1,1,3-trimethylindan-4-yl)-1-methyl-3-difluoromethylpyrazole-4-carboxylic acid amide in Reference Example 4.

FIG. 10 shows a DSC/TGA chart of (R)-(−)-N-(1,1,3-trimethylindan-4-yl)-1-methyl-3-difluoromethylpyrazole-4-carboxylic acid amide in Reference Example 4.

FIG. 11 shows an XRD chart of a hydrate of (R)-(−)-N-(1,1,3-trimethylindan-4-yl)-1-methyl-3-difluoromethylpyrazole-4-carboxylic acid amide in Reference Example 5.

FIG. 12 shows an FT-Raman spectrum of a hydrate of (R)-(−)-N-(1,1,3-trimethylindan-4-yl)-1-methyl-3-difluoromethylpyrazole-4-carboxylic acid amide in Reference Example 5.

FIG. 13 shows a DSC/TGA chart of a hydrate of (R)-(−)-N-(1,1,3-trimethylindan-4-yl)-1-methyl-3-difluoromethylpyrazole-4-carboxylic acid amide in Reference Example 5.

FIG. 14 shows an XRD chart of a 2-methoxyethanol/hydrate of (R)-(−)-N-(1,1,3-trimethylindan-4-yl)-1-methyl-3-difluoromethylpyrazole-4-carboxylic acid amide in Reference Example 7.

FIG. 15 shows an FT-Raman spectrum of a 2-methoxyethanol/hydrate of (R)-(−)-N-(1,1,3-trimethylindan-4-yl)-1-methyl-3-difluoromethylpyrazole-4-carboxylic acid amide in Reference Example 7.

FIG. 16 shows a DSC/TGA chart of a 2-methoxyethanol/hydrate of (R)-(−)-N-(1,1,3-trimethylindan-4-yl)-1-methyl-3-difluoromethylpyrazole-4-carboxylic acid amide in Reference Example 7.

FIG. 17 shows an XRD chart of a 1-propanol/cyclohexane/hydrate of (R)-(−)-N-(1,1,3-trimethylindan-4-yl)-1-methyl-3-difluoromethylpyrazole-4-carboxylic acid amide in Reference Example 9.

FIG. 18 shows an RT-Raman spectrum of a 1-propanol/cyclohexane/hydrate of (R)-(−)-N-(1,1,3-trimethylindan-4-yl)-1-methyl-3-difluoromethylpyrazole-4-carboxylic acid amide in Reference Example 9.

FIG. 19 shows a DSC/TGA chart of a 1-propanol/cyclohexane/hydrate of (R)-(−)-N-(1,1,3-trimethylindan-4-yl)-1-methyl-3-difluoromethylpyrazole-4-carboxylic acid amide in Reference Example 9.

FIG. 20 shows an XRD chart of a tetrahydrofuran/hydrate of (R)-(−)-N-(1,1,3-trimethylindan-4-yl)-1-methyl-3-difluoromethylpyrazole-4-carboxylic acid amide in Reference Example 11.

FIG. 21 shows an FT-Raman spectrum of a tetrahydrofuran/hydrate of (R)-(−)-N-(1,1,3-trimethylindan-4-yl)-1-methyl-3-difluoromethylpyrazole-4-carboxylic acid amide in Reference Example 11.

FIG. 22 shows a DSC/TGA chart of a tetrahydrofuran/hydrate of (R)-(−)-N-(1,1,3-trimethylindan-4-yl)-1-methyl-3-difluoromethylpyrazole-4-carboxylic acid amide in Reference Example 11.

FIG. 23 shows an XRD chart of a dimethylsulfoxide solvate of (R)-(−)-N-(1,1,3-trimethylindan-4-yl)-1-methyl-3-difluoromethylpyrazole-4-carboxylic acid amide in Reference Example 13.

FIG. 24 shows an FT-Raman spectrum of a dimethylsulfoxide solvate of (R)-(−)-N-(1,1,3-trimethylindan-4-yl)-1-methyl-3-difluoromethylpyrazole-4-carboxylic acid amide in Reference Example 13.

FIG. 25 shows a DSC/TGA chart of a dimethylsulfoxide solvate of (R)-(−)-N-(1,1,3-trimethylindan-4-yl)-1-methyl-3-difluoromethylpyrazole-4-carboxylic acid amide in Reference Example 13.

FIG. 26 shows an XRD chart of a xylene solvate of (R)-(−)-N-(1,1,3-trimethylindan-4-yl)-1-methyl-3-difluoromethylpyrazole-4-carboxylic acid amide in Reference Example 14.

FIG. 27 shows a TG/DTA chart of a xylene solvate of (R)-(−)-N-(1,1,3-trimethylindan-4-yl)-1-methyl-3-difluoromethylpyrazole-4-carboxylic acid amide in Reference Example 14.

DESCRIPTION OF EMBODIMENTS

The present invention relates to a method for producing (R)-1,1,3-trimethyl-4-aminoindane, including the steps (A), (B), and (C).

<Step (A)>

1,1,3-Trimethyl-4-aminoindane is represented by the following formula. Examples of the 1,1,3-trimethyl-4-aminoindane include 1,1,3-trimethyl-4-aminoindane usually having an optical purity of approximately 0% ee to 25% ee, and the 1,1,3-trimethyl-4-aminoindane preferably has an optical purity of approximately 0% ee to 10% ee, and more preferably has an optical purity of approximately 0% ee to 5% ee.

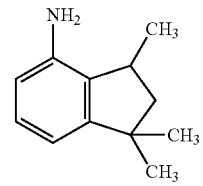

1,1,3-Trimethyl-4-aminoindane can be produced according to the method described in J. Chem. Soc. (C), 514 (1966), for example.

1,1,3-Trimethyl-4-aminoindane can be obtained by hydrogenating a compound represented by the formula (6) to obtain a compound represented by the formula (7); and reacting the compound represented by the formula (7) with an acid:

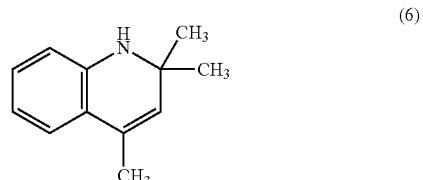

(6)

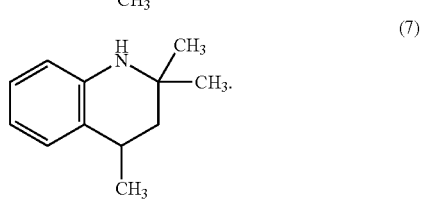

(7)

1,1,3-Trimethyl-4-aminoindane can be obtained by reacting a compound represented by the formula (6) with a protection reagent such as anhydrous acetic acid to obtain a compound represented by the formula (6) having its nitrogen atom protected with a protective group; hydrogenating the compound represented by the formula (6) having its nitrogen atom protected with a protective group to obtain a compound represented by the formula (7) having its nitrogen atom protected with a protective group the formula (7); and reacting the compound represented by the formula (7) having its nitrogen atom protected with a protective group the formula (7) with an acid.

As the acid, sulfuric acid is preferred. The concentration of the sulfuric acid is usually from 90% by weight to 98% by weight, and in view of a yield, the concentration is preferably from 92% by weight to 97% by weight.

The reaction of the compound represented by the formula (7) with an acid is carried out without a solvent and the reaction temperature is usually from 20° C. to 80° C.

After completion of the reaction, the obtained reaction mixture and water are mixed, the obtained mixture is neutralized with an alkali and extracted with an organic solvent insoluble in water, such as toluene, thereby obtaining a solution containing 1,1,3-trimethyl-4-aminoindane. The purity of 1,1,3-trimethyl-4-aminoindane is usually from 60% to 97%.

The compound represented by the formula (6) can be obtained by depolymerization of an oligomer of the compound represented by the formula (6).

Examples of the oligomer of the compound represented by the formula (6) include Antigen FR (manufactured by Sumitomo Chemical Co., Ltd.) and Antigen RD (manufactured by Sumitomo Chemical Co., Ltd.).

The depolymerization is carried out by reacting the compound represented by the formula (6) with an acid catalyst.

Examples of the acid catalyst include hydrochloric acid, sulfuric acid, nitric acid, tetrafluoroboric acid, p-toluenesulfonic acid, p-toluenesulfonic acid monohydrate, and the acid catalyst is preferably p-toluenesulfonic acid monohydrate.

The amount of the acid catalyst to be used is from usually from 0.1 parts by weight to 30 parts by weight, preferably from 0.1 parts by weight to 20 parts by weight, and more preferably from 1 part by weight to 10 parts by weight, with respect to 100 parts by weight of the oligomer of the compound represented by the formula (6).

The reaction temperature is usually from 100° C. to 250° C., preferably from 120° C. to 230° C., and more preferably from 140° C. to 200° C.

The reaction may be carried out at a normal pressure or under reduced pressure, and the reaction is preferably carried out under reduced pressure. In the case where the reaction is carried out under reduced pressure, the pressure is usually from 0.1 kPa to 10 kPa, preferably from 0.3 kPa to 7 kPa, and more preferably from 0.5 kPa to 5 kPa.

The depolymerization is preferably carried out while evaporating the obtained compound represented by the formula (6) from the reaction system. The compound thus obtained has relatively high purity.

The step (A) is preferably a step including the steps (A1), (A2), (A3), and (A4). More preferably, water is mixed into the reaction system prior to the step (A2).

<Step (A1)>

Examples of D-tartaric acid usually include commercially available products.

The amount of D-tartaric acid to be used is usually from 0.3 moles to 0.7 moles, preferably from 0.4 moles to 0.6 moles, and more preferably from 0.45 moles to 0.55 moles, with respect to 1 mole of 1,1,3-trimethyl-4-aminoindane.

The amount of methanol to be used is usually from 0.5 parts by weight to 3 parts by weight, preferably from 0.6 parts by weight to 2 parts by weight, and more preferably from 0.8 parts by weight to 2 parts by weight, with respect to 1 part by weight of 1,1,3-trimethyl-4-aminoindane.

The step (A1) may be carried out in the presence of water, and a solvent other than methanol and water, as necessary, in addition to methanol. Examples of the solvent other than methanol and water include an alcohol solvent other than methanol, such as ethanol and 2-propanol; an ether solvent such as tetrahydrofuran; a nitrile solvent such as acetonitrile; an ester solvent such as ethyl acetate; an aromatic hydrocarbon solvent such as toluene, xylene, and ethylbenzene; a halogenated aromatic hydrocarbon solvent such as monochlorobenzene; an aliphatic hydrocarbon solvent such as heptane and hexane; and an alicyclic hydrocarbon solvent such as cyclopentane and cyclohexane, and the solvent is preferably the aromatic hydrocarbon solvent.

These solvents may be combined and the total amount of the solvents other than methanol and water to be used is usually 10 parts by weight or less with respect to 1 part by weight of 1,1,3-trimethyl-4-aminoindane.

The amount of water to be used is usually from 0.01 parts by weight to 0.15 parts by weight, and preferably from 0.01 parts by weight to 0.1 parts by weight, with respect to 1 part by weight of 1,1,3-trimethyl-4-aminoindane.

The step (A1) is preferably carried out by mixing 1,1,3-trimethyl-4-aminoindane, D-tartaric acid, methanol, and water.

The mixing temperature is usually from 20° C. to 70° C., and preferably from 30° C. to 50° C.

For the mixing order, 1,1,3-trimethyl-4-aminoindane, D-tartaric acid, and methanol may be mixed at once; or D-tartaric acid and methanol may be mixed and then 1,1,3-trimethyl-4-aminoindane may be added to a mixture thus obtained. A mixture of D-tartaric acid and methanol may be added to 1,1,3-trimethyl-4-aminoindane. Alternatively, 1,1,3-trimethyl-4-aminoindane and methanol may be mixed, and D-tartaric acid may be added to a mixture thus obtained. Above all, D-tartaric acid is preferably added to a mixture of 1,1,3-trimethyl-4-aminoindane and methanol.

For the step (A1), in the case of mixing water, the mixing order is as follows: 1,1,3-trimethyl-4-aminoindane, D-tartaric acid, methanol, and water may be mixed at once; or D-tartaric acid, methanol, and water may be mixed, and then 1,1,3-trimethyl-4-aminoindane may be added to a mixture thus obtained. A mixture of D-tartaric acid, methanol, and water may be added to 1,1,3-trimethyl-4-aminoindane; or D-tartaric acid, methanol, and 1,1,3-trimethyl-4-aminoindane may be mixed and then water may be added to a mixture thus obtained. Further, 1,1,3-trimethyl-4-aminoindane, methanol, and water may be mixed and D-tartaric acid may be added to a mixture thus obtained. Above all, D-tartaric acid is preferably added to a mixture of 1,1,3-trimethyl-4-aminoindane, methanol, and water.

The addition may be carried out in one portion or in divided portions. In the case of adding D-tartaric acid to a mixture of 1,1,3-trimethyl-4-aminoindane and methanol, D-tartaric acid may be added in one portion, but they are preferably added in divided portions.

By mixing 1,1,3-trimethyl-4-aminoindane, D-tartaric acid, and methanol, a mixture including a methanol solvate of D-tartrate of (R)-1,1,3-trimethyl-4-aminoindane, and (S)-1,1,3-trimethyl-4-aminoindane and D-tartrate thereof is obtained. Depending on the amount of methanol to be used and the mixing temperature, a part of the methanol solvate of D-tartrate of (R)-1,1,3-trimethyl-4-aminoindane thus produced may be precipitated into the mixture in some cases.

(R)-1,1,3-Trimethyl-4-aminoindane is represented by the following formula:

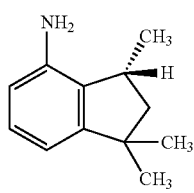

After the step (A1), a step in which methanol, and as necessary, a part of the solvent other than methanol are removed from the mixture obtained in the step (A1) may be included. The removal is usually carried out by concentrating the obtained mixture under reduced pressure. After removing methanol, and as necessary, a part of the solvent other than methanol, methanol, water, and a solvent other than methanol and water may be added to a residue of the mixture obtained in the step (A1).

<Step (A2)>

By cooling the mixture obtained in the step (A1), the methanol solvate of D-tartrate of (R)-1,1,3-trimethyl-4-aminoindane can be precipitated and the precipitated methanol solvate can be filtered to separate the methanol solvate of D-tartrate of (R)-1,1,3-trimethyl-4-aminoindane and the solution including (S)-1,1,3-trimethyl-4-aminoindane and D-tartrate thereof.

The temperature after cooling is a temperature lower than the mixing temperature in the step (A1), and it is preferably from −20° C. to 30° C., and more preferably from −10° C. to 20° C.

The cooling rate is usually from 1° C./hour to 10° C./hour, and by cooling the mixture obtained in the step (A1) with the cooling rate, crystals of the methanol solvate of D-tartrate of (R)-1,1,3-trimethyl-4-aminoindane are precipitated with high optical purity. The cooling rate is preferably from 1° C./hour to 8° C./hour, and more preferably from 3° C./hour to 6° C./hour.

The mixture obtained in the step (A1) may be mixed with water while cooling, and cooling may be stopped once and water may be added, followed by cooling again.

The withdrawn methanol solvate of D-tartrate of (R)-1,1,3-trimethyl-4-aminoindane is usually washed with at least one selected from the group consisting of methanol, water, and the solvent other than methanol and water, and as necessary, may be dried.

By mixing with water, the filtering property during withdrawing of the crystals of the methanol solvate of D-tartrate of (R)-1,1,3-trimethyl-4-aminoindane is improved.

<Step (A3)>

Examples of the alkali metal hydroxide include sodium hydroxide and potassium hydroxide, and examples of the alkali metal carbonate include sodium carbonate.

The amount of the aqueous alkali metal hydroxide solution or aqueous alkali metal carbonate solution to be used, in terms of alkali metals, is usually from 0.5 moles to 3 moles, with respect to 1 mole of D-tartaric acid used in the step (A1). The mixing temperature is usually from 10° C. to 80° C.

The concentration of the alkali metal hydroxide or the alkali metal carbonate in the aqueous alkali metal hydroxide solution or aqueous alkali metal carbonate solution is preferably such that the pH of the aqueous layer after mixing is 9 or more, and more preferably such that the pH is from 10 to 14.

The mixing of the aqueous alkali metal hydroxide solution or aqueous alkali metal carbonate solution may be carried out in the presence of an organic solvent. Examples of the organic solvent include an aromatic hydrocarbon solvent such as toluene, xylene, and ethylbenzene; a halogenated aromatic hydrocarbon solvent such as monochlorobenzene; an aliphatic hydrocarbon solvent such as heptane and hexane; an alicyclic hydrogen carbonate solvent such as cyclopentane and cyclohexane; an ether solvent such as diethyl ether and tert-butyl methyl ether; and an ester solvent such as ethyl acetate.

The amount of the organic solvent to be used is usually 10 parts by weight or less with respect to 1 part by weight of the methanol solvate.

For the mixing order, the methanol solvate of D-tartrate of (R)-1,1,3-trimethyl-4-aminoindane, the alkali metal hydroxide or aqueous alkali metal carbonate solution, and as necessary, the organic solvent may be mixed at once; or a mixture of the methanol solvate and as necessary, the organic solvent, the alkali metal hydroxide or aqueous alkali metal carbonate solution may be mixed. Alternatively, the methanol solvate may be added to a mixture of the aqueous alkali metal hydroxide solution or aqueous alkali metal carbonate solution, and as necessary, the organic solvent. Above all, the methanol solvate is preferably added to a mixture of the organic solvent and the alkali metal hydroxide or aqueous alkali metal carbonate solution.

After completion of the mixing, the obtained mixture can be subjected to liquid separation to withdraw (R)-1,1,3-trimethyl-4-aminoindane.

<Step (A4)>

The solution including (S)-1,1,3-trimethyl-4-aminoindane obtained in the step (A2) and D-tartrate thereof is concentrated, as necessary, and then mixed with an aqueous alkali metal hydroxide solution or aqueous alkali metal carbonate solution.

The step (A4) is the same as the step (A3) except that the solution including (S)-1,1,3-trimethyl-4-aminoindane obtained in the step (A2) and D-tartrate thereof is used instead of the methanol solvate of D-tartrate of (R)-1,1,3-trimethyl-4-aminoindane obtained in the step (A2).

The optical purity of the (S)-1,1,3-trimethyl-4-aminoindane obtained in the step (A4) is usually from 20% ee to 100% ee, and preferably from 50% ee to 100% ee.

<Step (B)>

The step (B) is preferably a step of bringing the (S)-1,1,3-trimethyl-4-aminoindane obtained in the step (A) or (C) into contact with a transition metal catalyst to perform racemization.

The optical purity of the 1,1,3-trimethyl-4-aminoindane obtained in the step (B) is usually from 0% ee to 25% ee, preferably from 0% ee to 10% ee, and more preferably from 0% ee to 5% ee.

Examples of the transition metal catalyst include a platinum catalyst such as platinum black, colloidal platinum, platinum oxide, and platinum-barium sulfate; a nickel catalyst such as reduced nickel, Urushihara nickel, nickel formate, Raney nickel, and nickel-diatomaceous earth; a palladium catalyst such as palladium-carbon, palladium-calcium carbonate, palladium-alumina, and palladium-platinum-carbon; a cobalt catalyst such as Raney cobalt; an iron catalyst such as Raney iron; and a copper catalyst such as copper chromite, and at least two kinds of the transition metal catalysts may be used. The transition metal catalyst is preferably a palladium catalyst, and more preferably palladium-carbon, palladium-alumina, or palladium-platinum-carbon.

The transition metal catalyst may be supported on a carrier. Examples of the carrier include activated carbon, silica, zeolite, and Celite (registered trademark).

The transition metal catalyst may be used after making the transition metal catalyst and hydrogen coexist to allow the transition metal catalyst absorb hydrogen, and the transition metal catalyst having hydrogen absorbed therein is preferred.

The amount of the transition metal catalyst to be used is usually from 0.0001 parts by weight to 1 part by weight, and preferably from 0.0005 parts by weight to 0.5 parts by weight, with respect to 1 part by weight of (S)-1,1, 3-trimethyl-4-aminoindane.

The contact between the transition metal catalyst and (S)-1,1,3-trimethyl-4-aminoindane may be carried out in the presence of a solvent or without a solvent.

Examples of the solvent include an aromatic solvent such as benzene, chlorobenzene, toluene, xylene, ethylbenzene, and pyridine; a halogen-containing hydrocarbon solvent such as chloroform and dichloromethane; an ester solvent such as ethyl acetate; a ketone solvent such as acetone, methyl ethyl ketone, and methyl isobutyl ketone; an ether solvent such as 1,2-dimethoxyethane, diethylene glycol dimethyl ether, polyethylene glycol, tetrahydrofuran, and dioxane; a nitrile solvent such as acetonitrile and propylnitrile; a sulfoxide solvent such as dimethylsulfoxide; an amide solvent such as dimethylacetamide and N-methylpyrrolidone; an alcohol solvent such as methanol, ethanol, and 2-propanol; an aqueous solvent such as water, an aqueous sodium hydroxide solution, and aqueous ammonia; and a mixed solvent thereof, and the solvent is preferably an alcohol solvent, and more preferably 2-propanol.

The amount of the solvent to be used is usually 100 parts by weight or less, and preferably 5 parts by weight or less, with respect to 1 part by weight of (S)-1,1,3-trimethyl-4-aminoindane.

The contact between the transition metal catalyst and (S)-1,1,3-trimethyl-4-aminoindane may also be carried out in the presence of an additive which will be a hydrogen source.

Examples of the additive include formic acid; formates such as ammonium formate and sodium formate; cyclohexene; a cyclohexene compound such as 3-methyl-1-cyclohexene and 4-methyl-1-cyclohexene; 1,3-cyclohexadiene; 1,4-cyclohexadiene; an octaline compound such as 1,2,3,4,4aα,5,8,8aβ-octahydronaphthalene, 1,2,3,4,5,6,7,8-octahydronaphthalene, 1-methyloctaline, and trans-2-methyloctaline; tetraline; 1,6-dimethyltetraline; 6-methyltetraline; limonene; pinene; 3-carene; phellandrene; terpinolene; 1-p-menthene; cadalene; pulegone; selinene; an alcohol compound such as methanol, ethanol, 2-propanol, and cyclohexanol; or a mixture thereof, preferably a cyclohexene compound, and more preferably cyclohexene.

The amount of the additive to be used is usually 10 parts by weight or less, preferably 5 parts by weight or less, and more preferably 2 parts by weight or less, with respect to 1 part by weight of (S)-1,1,3-trimethyl-4-aminoindane.

A compound in combination with an additive which will be a hydrogen source and a solvent may be used. The compound in combination with an additive which will be a hydrogen source and a solvent is preferably an alcohol compound, and more preferably 2-propanol.

The step (B) is more preferably a step in which a transition metal catalyst and (S)-1,1,3-trimethyl-4-aminoindane are mixed into the presence of hydrogen, and a mixture thus obtained is heated for racemization.

The contact between the transition metal catalyst and (S)-1,1,3-trimethyl-4-aminoindane may be carried out in a sealed container such as an autoclave or in an open container such as a flask. The contact between the transition metal catalyst and (S)-1,1,3-trimethyl-4-aminoindane can be carried out in the air, under a nitrogen atmosphere, or under a hydrogen atmosphere, and preferably under a nitrogen atmosphere or under a hydrogen atmosphere.

The contact temperature between the transition metal catalyst and (S)-1,1,3-trimethyl-4-aminoindane is usually from 20° C. to 250° C., preferably from 80° C. to 200° C., and more preferably from 100° C. to 190° C.

The contact between the transition metal catalyst and (S)-1,1,3-trimethyl-4-aminoindane is preferably carried out by mixing them at 50° C. to 80° C. and heating to 100° C. to 200° C., and preferably 150° C. to 200° C. under a hydrogen atmosphere, and more preferably carried out by mixing them at 50° C. to 80° C. under a hydrogen atmosphere, replacing hydrogen with nitrogen and then heating to 100° C. to 200° C., and preferably 150° C. to 200° C.

The contact time between the transition metal catalyst and (S)-1,1,3-trimethyl-4-aminoindane is usually from 0.1 hours to 100 hours, and preferably from 0.1 hours to 24 hours.

By removing the catalyst from the mixture obtained after the contact by filtration or the like, 1,1,3-trimethyl-4-aminoindane can be withdrawn. The obtained 1,1,3-trimethyl-4-aminoindane can also be purified by known methods such as concentration, extraction, transfer dissolution, recrystallization, and chromatography.

The catalyst removed by filtration or the like can be recovered and used again for the production of 1,1,3-trimethyl-4-aminoindane. Examples of the recovering method include a method of supporting to catalyst onto a carrier.

The recovered catalyst is preferably washed with a solvent. Examples of the solvent include an alcohol solvent such as methanol, ethanol, 2-propanol, and butanol; an aqueous alkali solution such as sodium hydroxide, potassium hydroxide, lithium hydroxide, and sodium carbonate; water; or a mixed solvent thereof.

<Step (C)>

The step (C) is the same as the step of obtaining (R)-1,1,3-trimethyl-4-aminoindane and (S)-1,1,3-trimethyl-4-aminoindane in the step (A) except that the 1,1,3-trimethyl-4-aminoindane obtained in the step (B) is used instead of 1,1,3-trimethyl-4-aminoindane.

The step (C) is preferably a step in which the 1,1,3-trimethyl-4-aminoindane obtained in the step (B) and the 1,1,3-trimethyl-4-aminoindane obtained in a step other than the step (B) are optically resolved to obtain (R)-1,1,3-trimethyl-4-aminoindane.

By repeating the step (B) and the step (C), (R)-1,1,3-trimethyl-4-aminoindane can be produced in a higher yield.

The production method of the present invention preferably includes the steps (A), (B'), (D), and (E). The step (A) is as described above.

<Step (B')>

The step (B') is the same as the step of obtaining 1,1,3-trimethyl-4-aminoindane in the step (B) except that the (S)-1,1,3-trimethyl-4-aminoindane obtained in the step (A) or step (E) is used instead of the (S)-1,1,3-trimethyl-4-aminoindane obtained in the step (A) or step (C).

<Step (D)>

The step (D) is preferably a step including the steps (D1), (D2), (D3), and (D4).

The step (D) may be a step of purifying the 1,1,3-trimethyl-4-aminoindane obtained in the step (B') and the 1,1,3-trimethyl-4-aminoindane obtained in the step other than the step (B').

<Step (D1)>

Examples of the organic solvent insoluble in water include an aliphatic hydrocarbon solvent such as hexane and heptane; an aromatic hydrocarbon solvent such as toluene, xylene, and ethylbenzene; a hydrophobic ester solvent such as ethyl acetate; a hydrophobic ether solvent such as diethyl ether, tert-butylmethyl ether, and methylcyclopentyl ether; and a hydrophobic ketone solvent such as methyl isobutyl ketone; and the aliphatic hydrocarbon solvent and the aromatic hydrocarbon solvent are preferred, and the aromatic hydrocarbon solvent is preferred.

The ratio of the amount of water to the amount of the organic solvent insoluble in water to be used (weight ratio; water/organic solvent insoluble in water) is usually from 1/99 to 99/1, preferably from 5/95 to 95/5, and more preferably from 10/90 to 90/10.

Examples of the hydrogen halide include hydrogen chloride, hydrogen bromide, and hydrogen iodide, and the hydrogen halide is preferably hydrogen chloride or hydrogen bromide, and more preferably hydrogen chloride. Hydrogen halide may be used as it is and may be in the form of an aqueous solution.

The amount of hydrogen halide to be used is usually from 1 mole to 2 moles with respect to 1 mole of 1,1,3-trimethyl-4-aminoindane.

The reaction of 1,1,3-trimethyl-4-aminoindane with hydrogen halide is usually carried out by mixing 1,1,3-trimethyl-4-aminoindane with hydrogen halide.

The reaction temperature is usually from 0° C. to 100° C., preferably from 5° C. to 90° C., and more preferably from 10° C. to 80° C.

The reaction time is usually from 0.1 hours to 24 hours, preferably from 0.1 hours to 12 hours, and more preferably from 0.1 hours to 6 hours.

<Step (D2)>

Separation is preferably carried out by leaving the mixture obtained in the step (D1) to stand and subjecting the mixture to a liquid separation treatment.

In the case where a layer having a hydrogen halide salt of the separated 1,1,3-trimethyl-4-aminoindane is an organic layer, the organic layer is washed with water, as necessary. In the case where a layer in which the hydrogen halide salt of the separated 1,1,3-trimethyl-4-aminoindane is dissolved is an aqueous layer, the aqueous layer is washed with the organic solvent insoluble in water, as necessary.

The amount of hydrogen halide in the step (D1) is 1.15 moles or more, and preferably 1.2 moles or more, with respect to 1 mole of 1,1,3-trimethyl-4-aminoindane, and the hydrogen halide salt of 1,1,3-trimethyl-4-aminoindane is usually dissolved in the organic layer. If the amount of hydrogen halide to be used is less than 1.15 moles with respect to 1 mole of 1,1,3-trimethyl-4-aminoindane, the hydrogen halide salt of 1,1,3-trimethyl-4-aminoindane is usually dissolved in the aqueous layer. Thus, by controlling the amount of hydrogen halide in the step (D1), the layer in which the hydrogen halide salt of 1,1,3-trimethyl-4-aminoindane is dissolved can be controlled.

In the case where the halide ion concentration of the mixture obtained in the step (D1) in the aqueous layer is 0.8 moles/L or more, the hydrogen halide salt of 1,1,3-trimethyl-4-aminoindane is usually dissolved in an organic layer. In the case where the halide ion concentration of the mixture obtained in the step (D1) in the aqueous layer is less than 0.8 moles/L, the hydrogen halide salt of 1,1,3-trimethyl-4-aminoindane is usually dissolved in an aqueous layer. Thus, by controlling the halide ion concentration in the aqueous layer of the mixture, a layer in which the hydrogen halide salt of 1,1,3-trimethyl-4-aminoindane is dissolved can be controlled. Examples of the method of controlling the halide ion concentration in the aqueous layer include a method in which the mixture obtained in the step (D1) and a water-soluble inorganic halide such as sodium chloride are mixed.

The temperature for separation of the layer in which the hydrogen halide salt of 1,1,3-trimethyl-4-aminoindane is dissolved and the other layer is usually from 0° C. to 100° C., preferably from 5° C. to 90° C., and more preferably from 10° C. to 80° C.

<Step (D3)>

The layer in which the hydrogen halide salt of 1,1,3-trimethyl-4-aminoindane is dissolved can be used as it is or can be concentrated and then cooled to withdraw the hydrogen halide salt of 1,1,3-trimethyl-4-aminoindane.

The cooling temperature is preferably a temperature which is lower than the separation temperature of the step (D2) by 5° C. or higher, more preferably from −15° C. to 50° C., still more preferably from −5° C. to 40° C., and particularly preferably from 0° C. to 30° C. The cooling time is usually from 1 minute to 24 hours.

<Step (D4)>

The precipitated hydrogen halide salt of 1,1,3-trimethyl-4-aminoindane can be withdrawn by filtering a mixture in which the salt is precipitated. The withdrawn hydrogen halide salt of 1,1,3-trimethyl-4-aminoindane is washed with a solvent, as necessary.

Examples of the base include ammonia; an alkali metal hydroxide such as lithium hydroxide, sodium hydroxide, and potassium hydroxide; an alkaline earth metal hydroxide such as magnesium hydroxide, calcium hydroxide, and barium hydroxide; an alkali metal hydrogen carbonate salt such as sodium hydrogen carbonate and potassium hydrogen carbonate; an alkali metal carbonate such as sodium carbonate and potassium carbonate; and an organic base such as trimethylamine, triethylamine, ethyldiisopropylamine, pyridine, and quinoline. Among these, ammonia, sodium hydroxide, potassium hydroxide, calcium hydroxide, barium hydroxide, sodium hydrogen carbonate, trimethylamine, triethylamine, and pyridine are preferred, ammonia, sodium hydroxide, potassium hydroxide, and sodium hydrogen carbonate are more preferred, and sodium hydroxide and potassium hydroxide are still more preferred. These bases may be used as they are or may be used in the form of a solution such as an aqueous solution.

The reaction of the hydrogen halide salt of 1,1,3-trimethyl-4-aminoindane with a base is usually carried out by mixing the both. The reaction is preferably carried out in water.

The amount of the base to be used is usually from 1 mole to 2 moles with respect to 1 mole of the hydrogen halide salt of 1,1,3-trimethyl-4-aminoindane.

The reaction temperature is usually from 0° C. to 100° C. The reaction time is usually from 0.1 hours to 5 hours.

After completion of the reaction, preferably, the reaction mixture and the organic solvent insoluble in water are mixed to obtain an organic layer and the organic layer is concentrated. The purity of the obtained 1,1,3-trimethyl-4-aminoindane is usually 97.5% or more.

<Step (E)>

The step (E) is the same as the step (C) except that the 1,1,3-trimethyl-4-aminoindane obtained in the step (D) is used instead of the 1,1,3-trimethyl-4-aminoindane obtained in the step (B).

By repeating the steps (B'), (D), and (E), (R)-1,1,3-trimethyl-4-aminoindane can be produced in a higher yield.

The present invention is directed to a method for producing a compound represented by the formula (1) (hereinafter sometimes referred to as a compound (1)), including the steps (A), (B), (C), and (F), and is preferably method for producing the compound (1), including the steps (A), (B'), (D), (E), and (F). The steps (A), (B), (C), (B'), (D), and (E) are described as above.

<Step (F)>

Examples of the halogen atom in $R^1$, $R^2$, and $R^3$ include a fluorine atom, a chlorine atom, a bromine atom, and an iodine atom.

Examples of the alkyl group which may be substituted with a halogen atom in $R^1$ and $R^2$ include an alkyl group having 1 to 6 carbon atoms, which may be substituted with a halogen atom, such as a methyl group, an ethyl group, an n-propyl group, an isopropyl group, an n-butyl group, a sec-butyl group, a tert-butyl group, an n-pentyl group, an n-hexyl group, a trifluoromethyl group, a difluoromethyl group, a monofluoromethyl group, a perfluoroethyl group, a perfluoro-n-propyl group, a perfluoroisopropyl group, a perfluoro-n-butyl group, a perfluorosec-butyl group, a perfluoro-tert-butyl group, a perfluoro-n-pentyl group, a perfluoro-n-hexyl group, a trichloromethyl group, a tribromomethyl group, and a triiodomethyl group.

$R^1$ is preferably a hydrogen atom or a methyl group, and more preferably a hydrogen atom.

$R^2$ is preferably a methyl group, a monofluoromethyl group, a difluoromethyl group, or a trifluoromethyl group, and more preferably a difluoromethyl group.

Examples of the alkoxy group which may be substituted with a halogen atom in $R^3$ include an alkoxy group having 1 to 6 carbon atoms, which may be substituted with a halogen atom, such as a methoxy group, an ethoxy group, an n-propoxy group, an isopropoxy group, an n-butoxy group, a sec-butoxy group, a tert-butoxy group, an n-pentyl oxy group, an n-hexyloxy group, a trifluoromethoxy group, a difluoromethoxy group, a perfluoroethoxy group, a perfluoro-n-propoxy group, a perfluoroisopropoxy group, a perfluoro-n-butoxy group, a perfluorosec-butoxy group, a perfluoro-tert-butoxy group, a perfluoro-n-pentyl oxy group, a perfluoro-n-hexyloxy group, a trichloromethoxy group, a tribromomethoxy group, and a triiodomethoxy group.

$R^3$ is preferably a chlorine atom, an ethoxy group, or a hydroxy group, and more preferably a chlorine atom.

Examples of the compound represented by the formula (2) (hereinafter sometimes referred to as a compound (2)) include ethyl 1-methyl-3-difluoromethylpyrazole-4-carboxylate, 1-methyl-3-difluoromethylpyrazole-4-carboxylic acid, and 1-methyl-3-difluoromethylpyrazole-4-carboxylic acid chloride.

Examples of the compound represented by the formula (1) (hereinafter sometimes referred to as a compound (1)) include (R)-(-)-N-(1,1,3-trimethylindan-4-yl)-1-methyl-3-difluoromethylpyrazole-4-carboxylic acid amide.

The step (F) is preferably a step (F-1), (F-2), (F-3), or (F-4).

<Step (F-1)>

The step (F-1) is a step in which (R)-1,1,3-trimethyl-4-aminoindane obtained in the step (C) or the step (E) is reacted with the compound (2) in which $R^3$ is a hydroxy group (hereinafter sometimes referred to as a compound (2-1)) in the presence of a dehydration-condensing agent to obtain the compound (1).

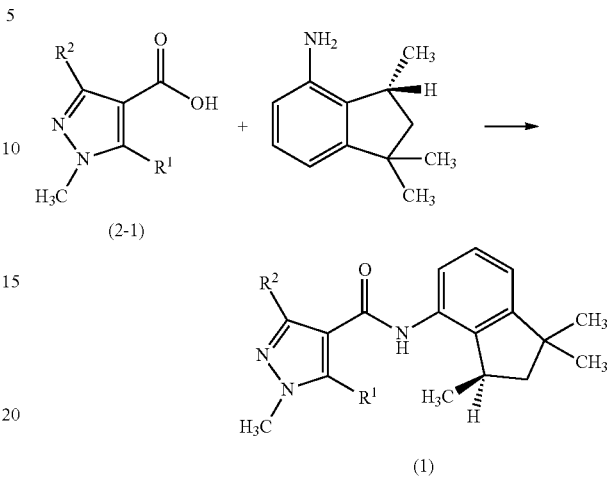

wherein $R^1$ and $R^2$ represent the same meanings.

Examples of the dehydration-condensing agent include a carbodiimide compound such as 1-ethyl-3-(3-dimethylaminopropyl)carbodiimide hydrochloride and 1,3-dicyclohexylcarbodiimide, and (benzotriazol-1-yloxy) tris(dimethylamino)phosphonium hexafluorophosphate.

The amount of the dehydration-condensing agent to be used is usually from 1 mole to 5 moles with respect to 1 mole of the compound (2-1).

The amount of (R)-1,1,3-trimethyl-4-aminoindane to be used is usually from 0.5 moles to 3 moles with respect to 1 mole of the compound (2-1).

The reaction of the compound (2-1) with (R)-1,1,3-trimethyl-4-aminoindane is usually carried out in the presence of a solvent inert to the reaction. Examples of the solvent include an ether solvent such as tetrahydrofuran, dioxane, ethylene glycol dimethyl ether, and tert-butylmethyl ether; an aliphatic hydrocarbon solvent such as hexane, heptane, and octane; an aromatic hydrocarbon solvent such as toluene, xylene, and ethylbenzene; a halogenated hydrogen carbonate solvent such as chlorobenzene; an ester solvent such as butyl acetate and ethyl acetate; a nitrile solvent such as acetonitrile; an acid amide solvent such as N,N-dimethylformamide; a sulfoxide solvent such as dimethylsulfoxide; a nitrogen-containing aromatic compound solvent such as pyridine; and a mixed solution thereof. The amount of the solvent to be used is usually from 1 part by weight to 20 parts by weight with 1 part by weight of the compound (2-1). The reaction temperature is usually from −20° C. to 150° C. and the reaction time is usually from 1 hour to 24 hours.

After completion of the reaction, the obtained reaction mixture, water, an aqueous sodium hydrogen carbonate solution, an aqueous sodium carbonate solution, an aqueous ammonium chloride solution, an aqueous sodium hydroxide solution, an aqueous potassium hydroxide solution, or an aqueous solution of an acid such as hydrochloric acid, sulfuric acid, phosphoric acid, and acetic acid are mixed, the solid is precipitated, and a mixture thus obtained is filtered to obtain the compound (1). In the case where the solid is not precipitated, the obtained mixture is extracted with an organic solvent and the organic layer is subjected to a post-treatment such as separation, drying, and concentration, to extract the compound (1). The organic layer may be washed with water; an aqueous alkali metal hydrogen carbonate salt solution such as an aqueous sodium hydrogen carbonate solution; an aqueous alkali metal carbonate solution such as an aqueous sodium carbonate solution; an aqueous ammonium chloride solution; an aqueous alkali metal hydroxide solution such as an aqueous sodium hydroxide solution and an aqueous potassium hydroxide solution; or an aqueous solution of an acid such as hydrochloric acid, sulfuric acid, phosphoric acid, and acetic acid. The washing of the organic layer is carried out at usually 0° C. to 70° C., and preferably 20° C. to 60° C. The withdrawn compound (1) can be further purified by column chromatography, recrystallization, or the like.

<Step (F-2)>

The step (F-2) is a step of reacting the (R)-1,1,3-trimethyl-4-aminoindane obtained in the step (C) or the step (E) with the compound (2-1) in the presence of a Lewis acid to obtain the compound (1).

Examples of the Lewis acid include a metal chloride such as titanium tetrachloride, zirconium tetrachloride, and aluminum chloride; a metal alkoxide compound such as titanium ethoxide, titanium propoxide, zirconium ethoxide, zirconium propoxide, aluminum ethoxide, aluminum propoxide, antimony ethoxide, and antimony propoxide; a metal amide compound such as tetrakis(dimethylamino)titanium, dichlorobis(dimethylamino)titanium and tetrakis(diethylamino)titanium; a borane compound such as borane, 3,5-bis(trifluoromethyl)phenyl boric acid, 2,4-bis(trifluoromethyl)phenyl boric acid, and pentafluorophenyl boric acid; and a borate compound such as triphenylmethyl tetrakis(pentafluorophenyl)borate, triphenylmethyl tetrakis(3,5-bistrifluoromethylphenyl)borate, and N,N-dimethylanilinium tetrakis(pentafluorophenyl)borate.

The amount of the Lewis acid to be used is usually from 0.001 moles to 3 moles with respect to 1 mole of the compound (2-1).

The amount of (R)-1,1,3-trimethyl-4-aminoindane to be used is usually from 0.5 moles to 3 moles with respect to 1 mole of the compound (2-1).

The reaction of the compound (2-1) with (R)-1,1,3-trimethyl-4-aminoindane is usually carried out in the presence of a solvent inert to the reaction. Examples of the solvent include the solvents mentioned in the step (F-1). The amount of the solvent to be used is usually from 1 part by weight to 20 parts by weight with respect to 1 part by weight of the compound (2-1). The reaction temperature is usually from −20° C. to 150° C. and the reaction time is usually from 1 hour to 120 hours. The reaction is preferably carried out while removing water thus by-produced.

After completion of the reaction, the treatment as in the step (F-1) can be carried out to withdraw the compound (1).

<Step (F-3)>

The step (F-3) is a step of reacting the (R)-1,1,3-trimethyl-4-aminoindane obtained in the step (C) or the step (E) with the compound (2) in which $R^3$ is an alkoxy group having 1 to 6 carbon atoms, which may be substituted with a halogen atom (hereinafter sometimes referred to as a compound (2-2)) in the presence of a Lewis acid or a Lewis base to obtain the compound (1).

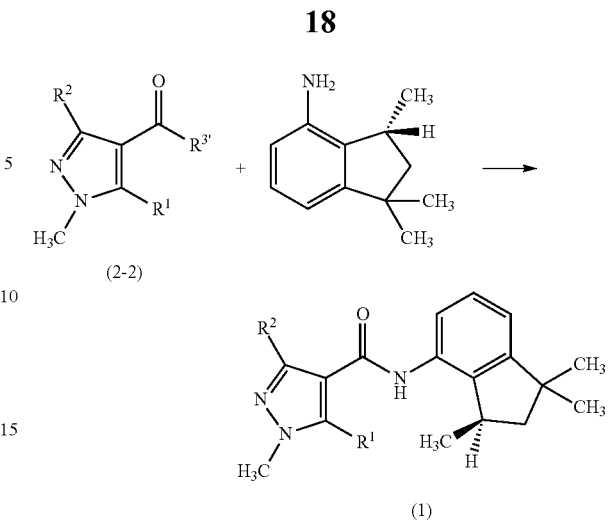

wherein $R^1$ and $R^2$ represent the same meanings as above and $R^{3'}$ represents an alkoxy group having 1 to 6 carbon atoms, which may be substituted with a halogen atom.

Examples of the Lewis acid include a metal chloride such as titanium tetrachloride, zirconium tetrachloride, and aluminum chloride; and a metal alkoxide compound such as titanium ethoxide, titanium propoxide, zirconium ethoxide, zirconium propoxide, aluminum ethoxide, aluminum propoxide, antimony ethoxide, and antimony propoxide.

The amount of the Lewis acid to be used is usually from 0.01 moles to 3 moles with respect to 1 mole of the compound (2-2).

The amount of (R)-1,1,3-trimethyl-4-aminoindane to be used is usually from 0.5 moles to 3 moles with respect to 1 mole of the compound (2-2).

Examples of the Lewis base include a metal alkoxide compound such as sodium methoxide, sodium ethoxide, sodium tert-butoxide, potassium methoxide, potassium ethoxide, and potassium tert-butoxide; a metal hydride such as sodium hydride; a lithium compound such as lithium diisopropyl amide and tert-butyl lithium; a silicon compound such as sodium hexamethyl disilazane and potassium hexamethyl disilazane; and an aluminum compound such as trimethyl aluminum, triethyl aluminum, and triisobutyl aluminum.

The amount of the Lewis base to be used is usually from 0.01 moles to 3 moles with respect to 1 mole of the compound (2-2).

The amount of (R)-1,1,3-trimethyl-4-aminoindane to be used is usually from 0.5 moles to 3 moles with respect to 1 mole of the compound (2-2).

The reaction of the compound (2-2) with (R)-1,1,3-trimethyl-4-aminoindane is usually carried out in the presence of a solvent inert to the reaction. Examples of the solvent include the solvents mentioned in the step (F-1). The amount of the solvent to be used is usually from 1 part by weight to 20 parts by weight with respect to 1 part by weight of the compound (2-2). The reaction temperature is usually from −20° C. to 150° C. and the reaction time is usually from 1 hour to 110 hours. The reaction is preferably carried out while removing alcohols thus by-produced.

After completion of the reaction, the treatment as in the step (F-1) can be carried out to withdraw the compound (1).

<Step (F-4)>

The step (F-4) is a step of reacting the (R)-1,1,3-trimethyl-4-aminoindane obtained in the step (C) or the step (E) with the compound (2) in which $R^3$ is a halogen atom (hereinafter sometimes referred to as a compound (2-3)) in the presence of a base to obtain the compound (1).

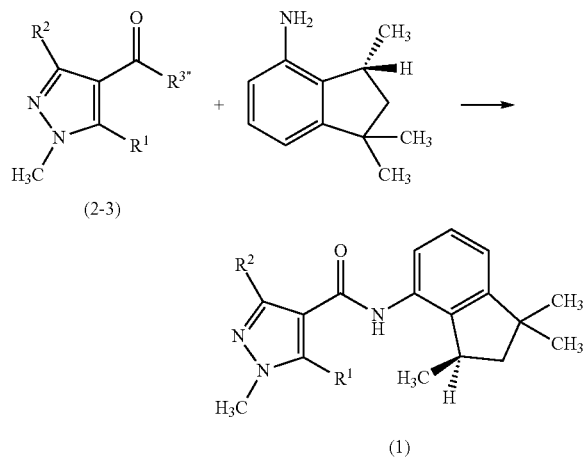

wherein $R^1$ and $R^2$ represent the same meanings as above and $R^{3''}$ represents a halogen atom.

Examples of the base include an alkali metal carbonate such as sodium carbonate and potassium carbonate; and a nitrogen-containing aromatic compound such as tertiary amines such as triethylamine and diisopropylethylamine, pyridine, and 4-dimethylaminopyridine.

The amount of the base to be used is usually from a catalytic amount to 5 moles, and preferably from 1 mole to 3 moles with respect to 1 mole of (R)-1,1,3-trimethyl-4-aminoindane.

The amount of the compound (2-3) to be used is usually from 0.5 moles to 1.5 moles, preferably from 0.8 moles to 1.3 moles, and more preferably from 1.0 mole to 1.2 moles, with respect to 1 mole of (R)-1,1,3-trimethyl-4-aminoindane.

The reaction of the compound (2-3) with (R)-1,1,3-trimethyl-4-aminoindane is usually carried out in the presence of a solvent. The solvent may be any one which is inert to the reaction, and examples thereof include an aliphatic hydrocarbon solvent such as pentane, hexane, heptane, octane, and cyclohexane; an aromatic hydrocarbon solvent such as toluene, xylene, and ethylbenzene; a halogenated aliphatic hydrocarbon solvent such as dichloromethane, chloroform, 1,2-dichloroethane, and carbon tetrachloride; a halogenated aromatic hydrocarbon solvent such as chlorobenzene, dichlorobenzene, and trichlorobenzene; an ether solvent such as diethyl ether, diisopropyl ether, tert-butylmethyl ether, cyclohexylmethyl ether, ethylene glycol dimethyl ether, tetrahydrofuran, and dioxane; an ester solvent such as ethyl acetate and butyl acetate; a nitrile solvent such as acetonitrile; and a mixed solution thereof, preferably an aromatic hydrocarbon solvent, a halogenated aromatic hydrocarbon solvent, and an ether solvent, and more preferably toluene, xylene, ethylbenzene, chlorobenzene, and tetrahydrofuran. The amount of the solvent to be used is preferably from 1 part by weight to 20 parts by weight, and more preferably from 2 parts by weight to 10 parts by weight, with respect to 1 part by weight of (R)-1,1,3-trimethyl-4-aminoindane.

The temperature for the reaction of the compound (2-3) with (R)-1,1,3-trimethyl-4-aminoindane is usually from −20° C. to 80° C., preferably from 0° C. to 70° C., and more preferably from 20° C. to 60° C. and the reaction time is usually from 0.1 hours to 24 hours.

After completion of the reaction, the treatment as in the step (F-1) can be carried out to withdraw the compound (1).

The present invention is directed to a method for producing the compound (1), including the steps (A), (B), (C), (G), and (H), and preferably a method for producing the compound (1), including the steps (A), (B'), (D), (E), (G), and (H). The steps (A), (B), (C), (B'), (D), and (E) are the same as described above.

<Step (G)>

The step (G) is preferably a step of reacting a compound represented by the formula (3) (hereinafter sometimes referred to as a compound (3)) with a chlorinating agent to obtain a compound represented by the formula (4) (hereinafter sometimes referred to as a compound (4)).

Examples of the chlorinating agent include thionyl chloride, oxalyl chloride, and phosgene. The amount of the chlorinating agent to be used is usually from 1 mole to 2 moles, and preferably from 1 mole to 1.5 moles, with respect to 1 mole of the compound (3).

The reaction of the compound (3) with the chlorinating agent can also be carried out in the presence of tertiary amine or amide. Examples of the tertiary amine or amide include pyridine, picoline, N,N-dimethylformamide, and N-methyl-N-phenylformamide. The amount of tertiary amine or amide to be used is usually from 0.001 moles to 0.05 moles, and preferably from 0.003 moles to 0.03 moles, with respect to 1 mole of the compound (3).

The reaction of the compound (3) with the chlorinating agent is usually carried out in the presence of a solvent. The solvent may be any one which is insert of the reaction, and examples thereof include an aliphatic hydrocarbon solvent such as pentane, hexane, heptane, and cyclohexane; an aromatic hydrocarbon solvent such as toluene, xylene, and ethylbenzene; a halogenated aliphatic hydrocarbon solvent such as dichloromethane, chloroform, 1,2-dichloroethane, and carbon tetrachloride; a halogenated aromatic hydrocarbon solvent such as chlorobenzene, dichlorobenzene, and trichlorobenzene; an ether solvent such as diethyl ether, diisopropyl ether, tert-butyl methyl ether, cyclohexylmethyl ether, ethylene glycol dimethyl ether, and dioxane; and a mixed solution thereof. The solvent is preferably the aromatic hydrocarbon solvent or the halogenated aromatic hydrocarbon solvent, and more preferably toluene, xylene, ethylbenzene, or chlorobenzene.

The amount of the solvent to be used is preferably from 0.5 parts by weight to 20 parts by weight, and more preferably from 1 part by weight to 10 parts by weight, with respect to 1 part by weight of the compound (3).

The reaction temperature between the compound (3) and the chlorinating agent is usually from 10° C. to 120° C., and preferably from 40° C. to 110° C., and the reaction time is usually from 0.1 hours to 24 hours.

After completion of the reaction, the obtained reaction mixture can be concentrated to obtain a compound (4). The obtained compound (4) may be purified by distillation or the like.

<Step (H)>

The step (H) is the same as the step (F-4) except that the compound (4) is used instead of the compound (2-3).

<Purification Step>

The withdrawn compound (1) can be further purified by column chromatography, recrystallization, or the like, and purification is preferred.

As the purification method, a method in which a compound (1) is dissolved in a solvent to prepare a solution and recrystallization is carried out using the solution is preferred. Seed crystals may be used in the recrystallization.

Examples of the solvent include an aliphatic hydrogen carbonate solvent such as pentane, hexane, heptane, octane, and cyclohexane; an aromatic hydrocarbon solvent such as toluene, xylene, and ethylbenzene; a halogenated aliphatic hydrogen carbonate solvent such as dichloromethane, chloroform, 1,2-dichloroethane, and carbon tetrachloride; a halogenated aromatic hydrocarbon solvent such as chlorobenzene, dichlorobenzene, and trichlorobenzene; an ether solvent such as diethyl ether, diisopropyl ether, tert-butylmethyl ether, cyclohexylmethyl ether, ethylene glycol dimethyl ether, tetrahydrofuran, and dioxane; an ester solvent such as ethyl acetate and butyl acetate; a nitrile solvent such as acetonitrile; an alcohol solvent such as methanol, ethanol, and 2-propanol; and a mixed solution thereof. The solvent is preferably the aliphatic hydrocarbon solvent, the aromatic hydrocarbon solvent, the halogenated aromatic hydrocarbon solvent, or the ester solvent, and more preferably toluene, xylene, ethylbenzene, hexane, heptane, or ethyl acetate.

EXAMPLES

"%" and "part(s)" in Examples are "% by weight" and "part(s) by weight" unless otherwise specified.

In Examples, the ratio of R isomers/S isomers was analyzed by means of high performance liquid chromatography (area percentage method) using chiral columns. The content of each of 1,1,3-trimethyl-4-aminoindane and (R)-(−)-N-(1,1,3-trimethylindan-4-yl)-1-methyl-3-difluoromethylpyrazole-4-carboxylic acid amide was analyzed by means of liquid chromatography (internal standard method).

In Examples, XRD was measured under the following conditions.

Example 3 and Reference Example 14

Device: SmartLab (Rigaku Corporation))
X-ray output: CuKα, 45 kV, 200 mA
Sampling width: 0.02°
Scanning range: 5° to 50°

Reference Examples 1 to 13

Device: X'Pert Pro diffractometer (PANalytical)
X-ray output: CuKα, 45 kV, 40 mA
Sampling width: 0.02°
Scanning range: 2° to 40°

In Examples, the FT-Raman spectrum was measured under the following conditions.

Device: Nicolet NXR9650 and NXR960 spectrometer (Thermo Electron)
Excitation laser: 1064 nm
Resolution: 4 cm$^{-1}$
Scanning number: 128
Apodization function: Happ-Genzel
Zero filling: 2 levels In Examples, thermal analysis (DSC) was measured under the following conditions.

Device: Q100 differential scanning calorimeter (TA instruments)
Atmosphere: nitrogen
Gas flow rate: 40 mL/min
Heating speed: 15° C./min In Examples, thermal analysis (TGA) was measured under the following conditions.

Device: Q500 thermogravimetric analyzer (TA instruments)
Atmosphere: nitrogen
Gas flow rate: 40 mL/min
Heating speed: 15° C./min In Examples, thermal analysis (TG-DTA) was measured under the following conditions.

Device: TG-DTA2000SR (BRUKER)
Atmosphere: nitrogen
Gas flow rate: 150 mL/min
Heating speed: 5° C./rain Example 1

<Step (A)>
[Step (A1)]

Under a nitrogen atmosphere, 80.5 parts (purity: 62.1%) of 1,1,3-trimethyl-4-aminoindane, 31.5 parts (0.63 parts with respect to 1 part of 1,1,3-trimethyl-4-aminoindane) of methanol, 2.0 parts (0.04 parts with respect to 1 part of 1,1,3-trimethyl-4-aminoindane) of water, and 9.5 parts of toluene were mixed at room temperature. The obtained mixture was warmed to 40° C. and then 6.5 parts (0.15 moles with respect to 1 mole of 1,1,3-trimethyl-4-aminoindane) of D-tartaric acid was added thereto. To the obtained mixture was added a small amount of seed crystals, followed by stirring for 1 hour, and then 15.1 parts (0.35 moles with respect to 1 mole of 1,1,3-trimethyl-4-aminoindane) of D-tartaric acid was added thereto in 7 divided portions at an interval of 10 minutes.

The obtained mixture was stirred at 40° C. for 3 hours, then cooled to 0° C. at a cooling rate of 5° C./hour, and stirred at 0° C. for 10 hours.

[Step (A2)]

The obtained mixture was filtered to obtain each of crystals and a filtrate.

The obtained crystals were washed sequentially once with 35.0 parts of a mixed solvent of ice-cooled methanol and toluene at 1:9 (weight ratio) and once with 50.0 parts of ice-cooled toluene to obtain each of a washing liquid and crystals.

The obtained crystals were dried under reduced pressure to obtain 39.9 parts of a methanol solvate of D-tartrate of (R)-1,1,3-trimethyl-4-aminoindane. The ratio of R isomers/S isomers of the methanol solvate of 1,1,3-trimethyl-4-aminoindane was 98.1/1.9.

The filtrate and the washing liquid were all recovered and mixed to obtain a solution including D-tartrate of (S)-1,1,3-trimethyl-4-aminoindane.

[Step (A3)]

To a solution formed by mixing 39.5 parts of xylene and 78.9 parts of a 14% aqueous sodium hydroxide solution was added 39.5 parts of the obtained methanol solvate of D-tartrate of (R)-1,1,3-trimethyl-4-aminoindane. The obtained mixture was stirred and subjected to liquid separation. The obtained organic layer was washed with water and then concentrated under reduced pressure to obtain 19.9 parts (content: 93.9%) of (R)-1,1,3-trimethyl-4-aminoindane. The yield from the step (A1) was 37.3%. The ratio of R isomers/S isomers of 1,1,3-trimethyl-4-aminoindane was 98.1/1.9.

[Step (A4)]

A solution formed by mixing 10.8 parts of a 24% aqueous sodium hydroxide solution and 41.7 parts of water was warmed to 30° C. To the obtained mixture was added dropwise 160.8 parts of a solution including the obtained D-tartrate of (S)-1,1,3-trimethyl-4-aminoindane (content of (S)-1,1,3-trimethyl-4-aminoindane: 17.6%) over 2 hours. The obtained mixture was stirred at 30° C. for 1 hour and subjected to liquid separation. The obtained organic layer was washed with water and then concentrated under reduced pressure to obtain 35.4 parts of (S)-1,1,3-trimethyl-4-aminoindane. The content of 1,1,3-trimethyl-4-aminoindane was 76.7%. Further, the ratio of R isomers/S isomers of 1,1,3-trimethyl-4-aminoindane was 17.7/82.3 (optical purity of 64.6% ee (S)).

<Step (B)>

To an autoclave reaction container were put 31.0 parts of the (S)-1,1,3-trimethyl-4-aminoindane obtained in the step (A), 3.25 parts of an E-type of 5% palladium (manufactured by N. E. CHEMCAT Corporation, 50% wet)—carbon, and 1.1 parts of water to obtain a mixture. The reaction container was sealed and the gas in the reaction container was replaced with nitrogen. While stirring the mixture, hydrogen was included into the reaction container until the inner pressure of hydrogen in the reaction container became 0.8 MPa, followed by stirring at an inner temperature of 80° C. for 3 hours. The gas in the reaction container was replaced with nitrogen and the mixture was stirred at an inner temperature of 180° C. and an inner pressure of 0.80 MPa for 24 hours. The obtained reaction mixture was cooled and filtered using Celite to obtain each of a solid and a filtrate. The obtained solid was washed with 10 parts of toluene to obtain a washing liquid. The obtained washing liquid and the obtained filtrate were mixed to obtain 37.9 parts of a solution of 1,1,3-trimethyl-4-aminoindane in toluene (content of 1,1,3-trimethyl-4-aminoindane: 54.6%). The 1,1,3-trimethyl-4-aminoindane had an optical purity of 0.90% ee and a recovery rate of 87.0%.

<Step (C)>

At room temperature under a nitrogen atmosphere, 33.0 parts of the solution of 1,1,3-trimethyl-4-aminoindane obtained in the step (B) in toluene, 27.9 parts (purity: 62.1%) of 1,1,3-trimethyl-4-aminoindane, 22.2 parts (0.63 parts with respect to 1 part of 1,1,3-trimethyl-4-aminoindane) of methanol, 1.4 parts (0.04 parts with respect to 1 part of 1,1,3-trimethyl-4-aminoindane) of water, and 9.5 parts of toluene were mixed. The obtained mixture was warmed to 40° C., and then 4.6 parts (0.15 moles with respect to 1 mole of 1,1,3-trimethyl-4-aminoindane) of D-tartaric acid was added thereto. To the obtained solution was added a small amount of seed crystals, followed by stirring for 1 hour, and then 10.7 parts (0.35 moles with respect to 1 mole of 1,1,3-trimethyl-4-aminoindane) of D-tartaric acid was added thereto in 7 divided portions at an interval of 10 minutes.

The obtained mixture was stirred at 40° C. for 3 hours, then cooled to 0° C. at a cooling rate of 5° C./hour, and further stirred at 0° C. for 8 hours. The obtained mixture was filtered to obtain each of crystals and a filtrate.

The obtained crystals were washed sequentially once with 24.7 parts of a mixed solvent of ice-cooled methanol and toluene at 1:9 (weight ratio) and once with 35.3 parts of ice-cooled toluene to obtain each of a washing liquid and crystals.

The obtained crystals were dried under reduced pressure to obtain 28.7 parts of a methanol solvate of D-tartrate of (R)-1,1,3-trimethyl-4-aminoindane. The ratio of R isomers/S isomers of 1,1,3-trimethyl-4-aminoindane of the methanol solvate was 97.8/2.2.

The filtrate and the washing liquid were all recovered and mixed to obtain a solution including D-tartrate of (S)-1,1,3-trimethyl-4-aminoindane and (S)-1,1,3-trimethyl-4-aminoindane.

To a solution formed by mixing of 28.0 parts of xylene and 56.0 parts of a 14% aqueous sodium hydroxide solution was added 28.0 parts of the obtained methanol solvate of D-tartrate of (R)-1,1,3-trimethyl-4-aminoindane. The obtained mixture was stirred and subjected to liquid separation. The obtained organic layer was washed with 28.0 parts of water and then concentrated under reduced pressure to obtain 14.9 parts of (R)-1,1,3-trimethyl-4-aminoindane. The content of 1,1,3-trimethyl-4-aminoindane was 90.0%. Further, the ratio of R isomers/S isomers of 1,1,3-trimethyl-4-aminoindane was 97.7/2.3.

The total amount of (R)-1,1,3-trimethyl-4-aminoindane obtained in the step (A) and the (R)-1,1,3-trimethyl-4-aminoindane obtained in the step (C) was 32.1 parts as a pure fraction, and the total yield of the steps (A), (B), and (C) was 47.7%.

Example 2

<Step (A)>

[Step (A1)]

At room temperature under a nitrogen atmosphere, 112.7 parts (purity: 62.1%) of 1,1,3-trimethyl-4-aminoindane, 44.1 parts (0.63 parts with respect to 1 part of 1,1,3-trimethyl-4-aminoindane) of methanol, 2.8 parts (0.04 parts with respect to 1 part of 1,1,3-trimethyl-4-aminoindane) of water, and 13.3 parts of toluene were mixed. The obtained mixture was warmed to 40° C. and then 9.1 parts (0.15 moles with respect to 1 mole of 1,1,3-trimethyl-4-aminoindane) of D-tartaric acid was added thereto to obtain a solution. To the obtained solution was added a small amount of seed crystals, followed by stirring for 1 hour, and 21.1 parts (0.35 moles with respect to 1 mole of 1,1,3-trimethyl-4-aminoindane) of D-tartaric acid was added thereto in 7 divided portions at an interval of 10 minutes.

The obtained mixture was stirred at 40° C. for 3 hours, then cooled to 0° C. at a cooling rate of 5° C./hour, and further stirred at 0° C. for 2 hours.

[Step (A2)]

The obtained mixture was filtered to obtain each of crystals and a filtrate.

The obtained crystals were washed sequentially once with 49.0 parts of a mixed solvent of ice-cooled methanol and toluene at 1:9 (weight ratio) and once with 70.0 parts of ice-cooled toluene to obtain each of a washing liquid and crystals.

The crystals after washing were dried under reduced pressure to obtain 56.7 parts of a methanol solvate of D-tartrate of (R)-1,1,3-trimethyl-4-aminoindane. The ratio of R isomers/S isomers of 1,1,3-trimethyl-4-aminoindane of the methanol solvate was 98.0/2.0.

The filtrate and the washing liquid were all recovered and mixed to obtain a solution including D-tartrate of (S)-1,1,3-trimethyl-4-aminoindane and (S)-1,1,3-trimethyl-4-aminoindane.

[Step (A3)]

To a solution formed by mixing of 56.0 parts of xylene and 111.9 parts of a 14% aqueous sodium hydroxide solution was added 56.0 parts of the obtained methanol solvate of D-tartrate of (R)-1,1,3-trimethyl-4-aminoindane. The obtained mixture was stirred and subjected to liquid separation. The obtained organic layer was washed with water and then concentrated under reduced pressure to obtain 27.5 parts (content: 97.3%) of (R)-1,1,3-trimethyl-4-aminoindane. The yield from the step (A1) was 38.2%. The ratio of R isomers/S isomers of 1,1,3-trimethyl-4-aminoindane was 98.0/2.0.

[Step (A4)]

A solution formed by mixing 14.4 parts of a 24% aqueous sodium hydroxide solution and 55.5 parts of water was warmed to 30° C. To the obtained mixture was added dropwise 188.9 parts (content of (S)-1,1,3-trimethyl-4-aminoindane: 21.2%) of a solution including the obtained D-tartrate of (S)-1,1,3-trimethyl-4-aminoindane over 2 hours and a half. The obtained mixture was stirred at 30° C. for 1 hour and subjected to liquid separation. The obtained organic layer was washed with 55.4 parts of water and then concentrated under reduced pressure to obtain 51.8 parts of (S)-1,1,3-trimethyl-4-aminoindane. The content of 1,1,3-trimethyl-4-aminoindane was 76.5%. Further, the ratio of R isomers/S isomers of 1,1,3-trimethyl-4-aminoindane was 17.4/82.6 (optical purity of 65.2% ee (S)).

<Step (B')>

Into an autoclave reaction container were put 47.0 parts of the (S)-1,1,3-trimethyl-4-aminoindane obtained in the step (A), 4.87 parts of an E-type of 5% palladium (manufactured by N. E. CHEMCAT Corporation, 50% wet)—carbon, and 1.5 parts of water to obtain a mixture. The reaction container was sealed and the gas in the reaction container was replaced with nitrogen. While stirring the mixture, hydrogen was included into the reaction container until the inner pressure of hydrogen in the reaction container became 0.8 MPa, followed by stirring at an inner temperature of 80° C. for 3 hours. The gas in the reaction container was replaced with nitrogen and the mixture was stirred at an inner temperature of 180° C. and an inner pressure of 0.85 MPa for 24 hours. The obtained reaction mixture was cooled and filtered using Celite to obtain each of a solid and a filtrate. The obtained solid was washed with 8 parts of toluene to obtain a washing liquid. The obtained washing liquid and the obtained filtrate were mixed to obtain 50.8 parts of a solution of 1,1,3-trimethyl-4-aminoindane in toluene (content of 1,1,3-trimethyl-4-aminoindane: 64.9%). The 1,1,3-trimethyl-4-aminoindane had an optical purity of 0.35% ee and a recovery rate of 91.7%.

<Step (D)>

Under a nitrogen atmosphere, 41.87 parts of the solution of 1,1,3-trimethyl-4-aminoindane obtained in the step (B') in toluene, 43.77 parts of 1,1,3-trimethyl-4-aminoindane (purity: 62.1%), 95.52 parts of toluene, and 24.46 parts of water were mixed. The obtained mixture was heated to 65° C. and then 41.98 parts of concentrated hydrochloric acid was added thereto. The obtained mixture was stirred at 65° C. for 1 hour and then separated into an aqueous layer and an organic layer in which hydrochloride of 1,1,3-trimethyl-4-aminoindane had been dissolved. The obtained organic layer was cooled to 10° C. while stirring, and the crystals of hydrochloride of 1,1,3-trimethyl-4-aminoindane were precipitated. The precipitated crystals were withdrawn by filtration to obtain hydrochloride of 1,1,3-trimethyl-4-aminoindane. The obtained hydrochloride of 1,1,3-trimethyl-4-aminoindane had been dissolved in hot water. To the obtained solution was added an aqueous sodium hydroxide solution. To the obtained mixture was added toluene, and then the organic layer was separated. The organic layer was washed with water and then concentrated under reduced pressure to obtain 73.74 parts of a solution of 1,1,3-trimethyl-4-aminoindane in toluene in the form of a pale brown liquid. The recovery rate was 93.1% and the content of 1,1,3-trimethyl-4-aminoindane was 99.4%.

<Step (E)>

At room temperature under a nitrogen atmosphere, 72.4 parts (content of 1,1,3-trimethyl-4-aminoindane: 99.4%) of the solution of 1,1,3-trimethyl-4-aminoindane obtained in the step (D) in toluene, 45.4 parts (0.63 parts of with respect to 1 part of 1,1,3-trimethyl-4-aminoindane) of methanol, 2.9 parts (0.04 parts of with respect to 1 part of 1,1,3-trimethyl-4-aminoindane) of water, and 57.2 parts of toluene were mixed. The obtained mixture was warmed to 40° C. and then D-tartaric acid 9.3 parts (0.15 moles of with respect to 1 mole of 1,1,3-trimethyl-4-aminoindane) was added thereto to obtain a solution. To the obtained solution was added a small amount of seed crystals, followed by stirring for 1 hour. Then, 21.8 parts (0.35 moles of with respect to 1 mole of 1,1,3-trimethyl-4-aminoindane) of D-tartaric acid was added thereto in 7 divided portions at an interval of 10 minutes.

The obtained mixture was stirred at 40° C. for 3 hours, then cooled to 0° C. at a cooling rate of 5° C./hour, and further stirred at 0° C. for 24 hours. The obtained mixture was filtered to obtain each of crystals and a filtrate. The obtained crystals were washed sequentially once with 50.4 parts of a mixed solvent of ice-cooled methanol and toluene at 1:9 (weight ratio) and then washed once with 72.0 parts of ice-cooled toluene to obtain each of a washing liquid and crystals. The crystals after washing were dried under reduced pressure to obtain 60.8 parts of a methanol solvate of D-tartrate of (R)-1,1,3-trimethyl-4-aminoindane.

To a solution formed by mixing of 121.6 parts of xylene and 121.5 parts of a 14% aqueous sodium hydroxide solution was added 60.8 parts of the obtained methanol solvate of D-tartrate of (R)-1,1,3-trimethyl-4-aminoindane. The obtained mixture was stirred and subjected to liquid separation. The obtained organic layer was washed with 91.2 parts of water and then concentrated under reduced pressure to obtain 32.5 parts of (R)-1,1,3-trimethyl-4-aminoindane. The content of 1,1,3-trimethyl-4-aminoindane was 91.3%. Further, the ratio of R isomers/S isomers of 1,1,3-trimethyl-4-aminoindane was 97.3/2.7 and the yield was 41.2%.

The total amount of the (R)-1,1,3-trimethyl-4-aminoindane obtained in the step (A) and the (R)-1,1,3-trimethyl-4-aminoindane obtained in the step (E) as a pure fraction was 56.4 parts, and the total yield of the steps (A), (B'), (D), and (E) was 58.0%.

Example 3

<Step (G)>

At room temperature under a nitrogen atmosphere, 14.0 parts of 1-methyl-3-difluoromethylpyrazole-4-carboxylic acid and 35.1 parts of xylene were mixed. The obtained mixture was heated at 100° C. To the obtained mixture was added dropwise 11.2 parts of thionyl chloride over 5 hours. The obtained mixture was stirred at 100° C. for 15 hours and then cooled to 40° C. Thionyl chloride and xylene were evaporated from the obtained reaction mixture under reduced pressure to obtain brown 1-methyl-3-difluoromethylpyrazole-4-carboxylic acid chloride.

<Step (H)>

14.6 parts of the (R)-1,1,3-trimethyl-4-aminoindane obtained in the step (C), 9.2 parts of triethylamine, and 38.1 parts of xylene were mixed to prepare a solution. To the obtained solution was added dropwise a solution in which 1-methyl-3-difluoromethylpyrazole-4-carboxylic acid chloride obtained in the step (G) had been dissolved in 13.2 parts of xylene at 45° C. to 50° C. over 2 hours. The obtained mixture was stirred at 45° C. to 50° C. for 15 hours. The obtained reaction mixture and a 20% aqueous sodium hydroxide solution were mixed and then the organic layer was separated. The obtained organic layer was washed sequentially with water, 18% hydrochloric acid, water, a 1% aqueous sodium hydroxide solution, and water, and then concentrated under a condition of reduced pressure to obtain 27.5 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 89.7% (a yield with respect to (R)-1,1,3-trimethyl-4-aminoindane of 98.5%). Further, the ratio of R isomers/S isomers of (R)-(−)-N-(1,1,3-trimethylindan-4-yl)-1-methyl-3-difluoromethylpyrazole-4-carboxylic acid amide was 97.7/2.3.

<Purification Step>

At room temperature under a nitrogen atmosphere, 27.5 parts of the obtained (R)-(−)-N-(1,1,3-trimethylindan-4-yl)-1-methyl-3-difluoromethylpyrazole-4-carboxylic acid amide, 22.0 parts of xylene, and 37.1 parts of heptane were mixed. The obtained mixture was heated at 75° C. to obtain a homogeneous solution. The obtained homogeneous solution was cooled to 63° C. and then 0.02 parts of seed crystals were added thereto, followed by stirring at 63° C. for 1 hour. The obtained mixture was cooled to −5° C. at cooling rate of 10° C./hour and stirred at −5° C. for 12 hours. The obtained mixture was filtered and the obtained solid was washed with 37.3 parts of ice-cooled heptane and then dried under reduced pressure to obtain 24.1 parts of white crystals of (R)-(−)-N-(1,1,3-trimethylindan-4-yl)-1-methyl-3-difluoromethylpyrazole-4-carboxylic acid amide. The recovery rate was 97.6% and the ratio of R isomers/S isomers was 98.2/1.8.

The XRD chart of the obtained white crystals of (R)-(−)-N-(1,1,3-trimethylindan-4-yl)-1-methyl-3-difluoromethylpyrazole-4-carboxylic acid amide is shown in FIG. 1.

Example 4

<Step (F-1)>

At room temperature under a nitrogen atmosphere, 79.4 parts of 1-methyl-3-difluoromethylpyrazole-4-carboxylic acid, 79.6 parts (R isomers/S isomers 100.0/0.0) of (R)-1,1,3-trimethyl-4-aminoindane, 113.0 parts of 1-ethyl-3-(3-dimethylaminopropyl)carbodiimide hydrochloride, 11.0 parts of dimethylaminopyridine, 203.7 parts of pyridine, and 1059.3 parts of dimethylformamide were mixed. The obtained mixture was stirred at 125° C. for 5 hours. The obtained reaction mixture was cooled to room temperature. The obtained mixture was added dropwise to a mixture of 2500 parts of ice water and 170 parts of 36% hydrochloric acid, followed by extraction with ethyl acetate three times. The obtained organic layer was washed sequentially with 5% hydrochloric acid, water, a 5% aqueous sodium hydroxide solution, water, saturated physiologicalsaline, and water, dried over magnesium sulfate, and then concentrated under reduced pressure to obtain 109.0 parts of (R)-(−)-N-(1,1,3-trimethylindan-4-yl)-1-methyl-3-difluoromethylpyrazole-4-carboxylic acid amide. The obtained product was purified by silica gel chromatography, recrystallized with ethyl acetate/hexane, and then dried under reduced pressure to obtain 78.3 parts of white crystals of (R)-(−)-N-(1,1,3-trimethylindan-4-yl)-1-methyl-3-difluoromethylpyrazole-4-carboxylic acid amide. The ratio of R isomers/S isomers was 100.0/0.0 and the purity was 99.9%.

Example 5

<Step (F-2)>

At room temperature under a nitrogen atmosphere, (R)-1,1,3-trimethyl-4-aminoindane 4.39 parts (purity: 90.7%, R isomers/S isomers=96.0/4.0), 2.02 parts (purity: 99.0%) of 1-methyl-3-difluoromethylpyrazole-4-carboxylic acid, 6.07 parts of xylene, and 0.29 parts (purity: 99%) of antimony (III) ethoxide were mixed. Water was removed from the obtained mixture using a Dean-Stark apparatus and the residue was heated and refluxed for 60 hours. The obtained reaction liquid was cooled to room temperature. The yield of (R)-(−)-N-(1,1,3-trimethylindan-4-yl)-1-methyl-3-difluoromethylpyrazole-4-carboxylic acid amide with respect to 1-methyl-3-difluoromethylpyrazole-4-carboxylic acid was 75.9%. Further, the ratio of R isomers/S isomers of (R)-(−)-N-(1,1,3-trimethylindan-4-yl)-1-methyl-3-difluoromethylpyrazole-4-carboxylic acid amide was 96.0/4.0.

Example 6

<Step (F-2)>

At room temperature under a nitrogen atmosphere, 6.58 parts (purity: 90.7%, R isomers/S isomers=96.0/4.0) of (R)-1,1,3-trimethyl-4-aminoindane, 3.03 parts (purity: 99.0%) of 1-methyl-3-difluoromethylpyrazole-4-carboxylic acid, 9.10 parts of toluene, and 0.44 parts of 3,5-bis(trifluoromethyl)phenyl boric acid were mixed.

Water was removed from the obtained mixture using a Dean-Stark apparatus and the residue was heated and refluxed for 120 hours. The obtained reaction liquid was cooled to room temperature. The yield of (R)-(−)-N-(1,1,3-trimethylindan-4-yl)-1-methyl-3-difluoromethylpyrazole-4-carboxylic acid amide with respect to 1-methyl-3-difluoromethylpyrazole-4-carboxylic acid was 78.4%. Further, the ratio of R isomers/S isomers of (R)-(−)-N-(1,1,3-trimethylindan-4-yl)-1-methyl-3-difluoromethylpyrazole-4-carboxylic acid amide was 96.0/4.0.

Example 7

<Step (F-2)>

At room temperature under a nitrogen atmosphere, 6.59 parts (purity: 90.7%, R isomers/S isomers=96.0/4.0) of (R)-1,1,3-trimethyl-4-aminoindane, 3.03 parts (purity: 99.0%) of 1-methyl-3-difluoromethylpyrazole-4-carboxylic acid, 9.11 parts of toluene, and 0.11 parts (purity: 99.5%) of boric acid were mixed. Water was removed from the obtained mixture using a Dean-Stark apparatus and the residue was heated and refluxed for 96 hours. The obtained reaction liquid was cooled to room temperature. The yield of (R)-(−)-N-(1,1,3-trimethylindan-4-yl)-1-methyl-3-difluoromethylpyrazole-4-carboxylic acid amide with respect to 1-methyl-3-difluoromethylpyrazole-4-carboxylic acid was 71.3%. Further, the ratio of R isomers/S isomers of (R)-(−)-N-(1,1,3-trimethylindan-4-yl)-1-methyl-3-difluoromethylpyrazole-4-carboxylic acid amide was 96.0/4.0.

Example 8

<Step (F-3)>

At room temperature under a nitrogen atmosphere, 5.91 parts (purity: 95.9%, R isomers/S isomers=95.4/4.6) of (R)-1,1,3-trimethyl-4-aminoindane, 6.13 parts (purity: 97.8%) of ethyl 1-methyl-3-difluoromethylpyrazole-4-carboxylate, and 30.7 parts of tetrahydrofuran were mixed and stirred. To the obtained mixture was added 1.75 parts of sodium methoxide. The obtained mixture was heated in an oil bath at 90° C. and stirred for 10 hours while tetrahydrofuran was evaporated. At this time, tetrahydrofuran in the same amount of the evaporated tetrahydrofuran was added thereto freshly at times, such that the concentration of the reaction liquid became constant. The obtained mixture was cooled to room temperature and then 92.0 parts of toluene was added thereto. The obtained mixture was washed sequentially with 5% hydrochloric acid, a saturated sodium bicarbonate solution, and saturated physiological saline. The obtained organic layer was concentrated under reduced pressure to obtain 12.7 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 65.7% (the yield with respect to ethyl 1-methyl-3-difluoromethylpyrazole-4-carboxylate of 85.0%). Further, the ratio of R isomers/S isomers of (R)-(−)-N-(1,1,3-trimethylindan-4-yl)-1-methyl-3-difluoromethylpyrazole-4-carboxylic acid amide was 95.7/4.3.

Example 9

<Step (F-3)>

At room temperature under a nitrogen atmosphere, 5.91 parts (purity: 95.9%, R isomers/S isomers=95.4/4.6) of (R)-1,1,3-trimethyl-4-aminoindane, 21.5 parts of tetrahydrofuran, and 1.29 parts (purity: 60%) of sodium hydride were mixed. The obtained mixture was heated and refluxed for 1 hour. The reaction liquid was cooled to room temperature. To the obtained solution was added dropwise a solution in which 6.13 parts (purity: 97.8%) of ethyl 1-methyl-3-difluoromethylpyrazole-4-carboxylate had been dissolved in 9.2 parts of tetrahydrofuran. The obtained mixture was heated in an oil bath at 90° C. and stirred for 8 hours while tetrahydrofuran was evaporated. At this time, tetrahydrofuran in the same amount of the evaporated tetrahydrofuran was added thereto freshly at times, such that the concentration of the reaction liquid became constant. The obtained mixture was cooled to room temperature and then 92.0 parts of toluene was added thereto. The obtained mixture was washed sequentially with 5% hydrochloric acid, a saturated sodium bicarbonate solution, and saturated physiological saline. The obtained organic layer was concentrated under reduced pressure to obtain 13.1 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 64.8% (the yield with respect to ethyl 1-methyl-3-difluoromethylpyrazole-4-carboxylate of 86.4%). Further, the ratio of R isomers/S isomers of (R)-(−)-N-(1,1,3-trimethylindan-4-yl)-1-methyl-3-difluoromethylpyrazole-4-carboxylic acid amide was 95.4/4.6.

Example 10

<Step F-3>

At room temperature under a nitrogen atmosphere, 5.92 parts (purity: 95.9%, R isomers/S isomers=95.4/4.6) of (R)-1,1,3-trimethyl-4-aminoindane, 42.9 parts of toluene, and 2.59 parts (purity: 60%) of sodium hydride were mixed. The obtained mixture was heated and refluxed for 1 hour. The obtained reaction liquid was cooled to room temperature. To the obtained solution was added dropwise a solution in which 6.13 parts (purity: 97.8%) of ethyl 1-methyl-3-difluoromethylpyrazole-4-carboxylate had been dissolved in 18.4 parts of toluene. The obtained mixture was heated and refluxed for 2 hours. The obtained reaction liquid was cooled to room temperature, and then 30.7 parts of toluene was added thereto. The organic layer was washed sequentially with 5% hydrochloric acid, a saturated sodium bicarbonate solution, and saturated physiological saline. The obtained organic layer was concentrated under reduced pressure to obtain 14.7 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 54.5% (the yield with respect to ethyl 1-methyl-3-difluoromethylpyrazole-4-carboxylate of 81.6%). Further, the ratio of R isomers/S isomers of (R)-(−)-N-(1,1,3-trimethylindan-4-yl)-1-methyl-3-difluoromethylpyrazole-4-carboxylic acid amide was 95.6/4.4.

Example 11

<Step F-3>

At room temperature under a nitrogen atmosphere, 5.02 parts (purity: 98.5%) of ethyl 1-methyl-3-difluoromethylpyrazole-4-carboxylate, 7.00 parts (purity: 90.7%, R isomers/S isomers=97.6/2.4) of (R)-1,1,3-trimethyl-4-aminoindane, and 20.3 parts of xylene were mixed, followed by stirring. To the obtained mixture was added 1.12 parts of titanium (IV) ethoxide. The obtained mixture was heated in an oil bath at 150° C. and stirred for hours while xylene was evaporated. At this time, xylene in the same amount of the evaporated xylene was added thereto freshly at times, such that the concentration of the reaction liquid became constant. The obtained mixture was cooled to room temperature and washed sequentially with water, 10% hydrochloric acid, a 10% aqueous sodium hydroxide solution, and water. The obtained organic layer was concentrated under reduced pressure to obtain 10.98 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 58.6% (the yield with respect to ethyl 1-methyl-3-difluoromethylpyrazole-4-carboxylate of 80.0%). Further, the ratio of R isomers/S isomers of (R)-(−)-N-(1,1,3-trimethylindan-4-yl)-1-methyl-3-difluoromethylpyrazole-4-carboxylic acid amide was 97.8/2.2.

Example 12

<Step (F-3)>

At room temperature under a nitrogen atmosphere, 5.01 parts (purity: 98.5%) of ethyl 1-methyl-3-difluoromethylpyrazole-4-carboxylate, 7.01 parts (purity: 90.7%, R isomers/S isomers=97.6/2.4) of (R)-1,1,3-trimethyl-4-aminoindane, and 20.2 parts of xylene were mixed and stirred. To the obtained mixture was added 1.04 parts of titanium (IV) propoxide. The obtained mixture was heated in an oil bath at 150° C. and stirred for 24 hours while xylene was evaporated. At this time, xylene in the same amount of the evaporated xylene was added thereto freshly at times, such that the concentration of the reaction liquid became constant. The obtained mixture was cooled to room temperature and washed sequentially with water, 10% hydrochloric acid, a 10% aqueous sodium hydroxide solution, and water. The obtained organic layer was concentrated under reduced pressure to obtain 11.37 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 55.9% (the yield with respect to ethyl 1-methyl-3-difluoromethylpyrazole-4-carboxylate of 79.1%). Further, the ratio of R isomers/S isomers of (R)-(−)-N-(1,1,3-trimethylindan-4-yl)-1-methyl-3-difluoromethylpyrazole-4-carboxylic acid amide was 97.8/2.2.

Example 13

<Step (F-3)>

At room temperature under a nitrogen atmosphere, 3.02 parts (purity: 98.5%) of ethyl 1-methyl-3-difluoromethylpyrazole-4-carboxylate, 4.22 parts (purity: 90.7%, R isomers/S isomers=97.6/2.4) of (R)-1,1,3-trimethyl-4-aminoindane, and 12.2 parts of xylene were mixed and stirred. To the obtained mixture was added 0.75 parts of antimony (III) ethoxide. The obtained mixture was heated in an oil bath at 150° C. and stirred for 110 hours while xylene was evaporated. At this time, xylene in the same amount of the evaporated xylene was added thereto freshly at times, such that the concentration of the reaction liquid became constant. The obtained mixture was cooled to room temperature and then filtered using Celite. The obtained organic layer was washed sequentially with water, 10% hydrochloric acid, a 10% aqueous sodium hydroxide solution, and water. The obtained organic layer was concentrated under reduced pressure to obtain 6.04 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 69.1% (the yield with respect to ethyl 1-methyl-3-difluoromethylpyrazole-4-carboxylate of 86.3%). Further, the ratio of R isomers/S isomers of (R)-(−)-N-(1,1,3-trimethylindan-4-yl)-1-methyl-3-difluoromethylpyrazole-4-carboxylic acid amide was 97.8/2.2.

Example 14

<Step (F-3)>

At room temperature under a nitrogen atmosphere, 3.01 parts (purity: 98.5%) of ethyl 1-methyl-3-difluoromethylpyrazole-4-carboxylate, 4.21 parts (purity: 90.7%, R isomers/S isomers=97.6/2.4) of (R)-1,1,3-trimethyl-4-aminoindane, and 21.3 parts of chlorobenzene were mixed and stirred. To the obtained mixture was added 2.36 parts of aluminum (III) ethoxide. The obtained mixture was heated in an oil bath at 150° C. and stirred for 82 hours while chlorobenzene was evaporated. At this time, chlorobenzene in the same amount of the evaporated chlorobenzene was added thereto freshly at times, such that the concentration of the reaction liquid became constant. The obtained mixture was cooled to room temperature and then filtered using Celite. The obtained organic layer was washed sequentially with water, 10% hydrochloric acid, a 10% aqueous sodium hydroxide solution, and water. The obtained organic layer was concentrated under reduced pressure to obtain 6.50 parts of (R)-(−)-N-(1,1,3-trimethylindan-4-yl)-1-methyl-3-difluoromethylpyrazole-4-carboxylic acid amide. The content of (R)-(−)-N-(1,1,3-trimethylindan-4-yl)-1-methyl-3-difluoromethylpyrazole-4-carboxylic acid amide was 35.0% (the yield with respect to ethyl 1-methyl-3-difluoromethylpyrazole-4-carboxylate of 47.0%). Further, the ratio of R isomers/S isomers of (R)-(−)-N-(1,1,3-trimethylindan-4-yl)-1-methyl-3-difluoromethylpyrazole-4-carboxylic acid amide was 97.7/2.3.

Reference Example 1

The XRD chart, the FT-Raman spectrum, and the DSC/TGA chart of the white crystals of (R)-(−)-N-(1,1,3-trimethylindan-4-yl)-1-methyl-3-difluoromethylpyrazole-4-carboxylic acid amide (a ratio of R isomers/S isomers of 100.0/0.0) synthesized by carrying out the same operation as in Example 3, are shown in FIG. 2, FIG. 3, and FIG. 4, respectively.

Reference Example 2

To 180 mg of the (R)-(−)-N-(1,1,3-trimethylindan-4-yl)-1-methyl-3-difluoromethylpyrazole-4-carboxylic acid amide synthesized in Reference Example 1 was added 250 µL of ethanol/water (volume ratio: 95/5). The obtained suspension was stirred for 40 hours while repeating warming and cooling within a range from 30° C. to 5° C. The obtained suspension was filtered and the obtained filtrate was cooled to 4° C. for 5 days and then cooled to −20° C. for hours. The obtained solution was warmed to room temperature and then the solvent was slowly concentrated for 6 days. The obtained mixture was filtered and the obtained solid was dried in air for 1 hour to obtain a solid of the ethanol/hydrate of (R)-(−)-N-(1,1,3-trimethylindan-4-yl)-1-methyl-3-difluoromethylpyrazole-4-carboxylic acid amide. The XRD chart, the FT-Raman spectrum, and the DSC/TGA chart of the obtained solid are shown in FIG. 5, FIG. 6, and FIG. 7, respectively.

Reference Example 3

To 150 mg of the (R)-(−)-N-(1,1,3-trimethylindan-4-yl)-1-methyl-3-difluoromethylpyrazole-4-carboxylic acid amide synthesized in Reference Example 1 was added 200 µL of ethanol/water (volume ratio: 95/5). The obtained suspension was stirred at 50° C. for 30 minutes to obtain a homogeneous solution. The obtained solution was filtered in a container having 1 mg of the ethanol/hydrate of (R)-(−)-N-(1,1,3-trimethylindan-4-yl)-1-methyl-3-difluoromethylpyrazole-4-carboxylic acid amide obtained in Reference Example 2, and the obtained suspension was stirred at room temperature for 1 hour. The obtained mixture was filtered and then the obtained solid was dried in air for 1 hour to obtain a solid of the ethanol/hydrate of (R)-(−)-N-(1,1,3-trimethylindan-4-yl)-1-methyl-3-difluoromethylpyrazole-4-carboxylic acid amide. The XRD chart of the obtained solid was the same as in FIG. 5.

Reference Example 4

20 mg of the solid of the ethanol/hydrate of (R)-(−)-N-(1,1,3-trimethylindan-4-yl)-1-methyl-3-difluoromethylpyrazole-4-carboxylic acid amide obtained in Reference Example 2 was dried at 50° C. for 24 hours while bubbling with nitrogen under reduced pressure. The XRD chart, the FT-Raman spectrum, and the DSC/TGA chart of the obtained solid of (R)-(−)-N-(1,1,3-trimethylindan-4-yl)-1-methyl-3-difluoromethylpyrazole-4-carboxylic acid amide are shown in FIG. 8, FIG. 9, and FIG. 10, respectively.

Reference Example 5

20 mg of the solid of the ethanol/hydrate of (R)-(−)-N-(1,1,3-trimethylindan-4-yl)-1-methyl-3-difluoromethylpyrazole-4-carboxylic acid amide obtained in Reference Example 2 was left to stand for 48 hours. The XRD chart, the FT-Raman spectrum, and the DSC/TGA chart of the obtained hydrate of (R)-(−)-N-(1,1,3-trimethylindan-4-yl)-1-methyl-3-difluoromethylpyrazole-4-carboxylic acid amide are shown in FIG. 11, FIG. 12, and FIG. 13 respectively.

Reference Example 6

To 60 mg of the (R)-(−)-N-(1,1,3-trimethylindan-4-yl)-1-methyl-3-difluoromethylpyrazole-4-carboxylic acid amide synthesized in Reference Example 1 was added 750 μL of hexane and 30 μL of 2-methoxyethanol. The obtained suspension was stirred for 40 hours while repeating warming and cooling within a range from 30° C. to 5° C. The obtained mixture was filtered and the obtained solid was dried in air for 3 hours to obtain a solid of the 2-methoxyethanol/hydrate of (R)-(−)-N-(1,1,3-trimethylindan-4-yl)-1-methyl-3-difluoromethylpyrazole-4-carboxylic acid amide. The XRD chart of the obtained solid was the same as in FIG. 14.

Reference Example 7

To 60 mg of the (R)-(−)-N-(1,1,3-trimethylindan-4-yl)-1-methyl-3-difluoromethylpyrazole-4-carboxylic acid amide synthesized in Reference Example 1 were added 800 μL of hexane and 30 μL of 2-methoxyethanol. The obtained suspension was stirred at 30° C. for 1 hour. The obtained suspension was cooled to 5° C. and 2 mg of the 2-methoxyethanol/hydrate of (R)-(−)-N-(1,1,3-trimethylindan-4-yl)-1-methyl-3-difluoromethylpyrazole-4-carboxylic acid amide obtained in Reference Example 6 was added thereto, followed by stirring for 20 hours. The obtained mixture was filtered and the obtained solid was dried in air for 3 hours to obtain a solid of the 2-methoxyethanol/hydrate of (R)-(−)-N-(1,1,3-trimethylindan-4-yl)-1-methyl-3-difluoromethylpyrazole-4-carboxylic acid amide. The XRD chart, the FT-Raman spectrum, and the DSC/TGA chart of the obtained solid are shown in FIG. 14, FIG. 15, and FIG. 16, respectively.

Reference Example 8

To 120 mg of the (R)-(−)-N-(1,1,3-trimethylindan-4-yl)-1-methyl-3-difluoromethylpyrazole-4-carboxylic acid amide synthesized in Reference Example 1 were added 750 μL of cyclohexane and 60 μL of 1-propanol. The obtained suspension was stirred for 40 hours while repeating warming and cooling within a range from 30° C. to 5° C. The obtained suspension was filtered and the obtained filtrate was cooled to 4° C. for 5 days and cooled to −20° C. for 24 hours. The obtained mixture was filtered and the obtained solid was dried in air for 1 hour to obtain a solid of the 1-propanol/cyclohexane/hydrate of (R)-(−)-N-(1,1,3-trimethylindan-4-yl)-1-methyl-3-difluoromethylpyrazole-4-carboxylic acid amide. The XRD chart of the obtained solid is the same as in FIG. 17.

Reference Example 9

To 151 mg of the (R)-(−)-N-(1,1,3-trimethylindan-4-yl)-1-methyl-3-difluoromethylpyrazole-4-carboxylic acid amide synthesized in Reference Example 1 were added 750 μL of cyclohexane and 60 μL of 1-propanol. The obtained suspension was stirred at 50° C. for 70 minutes to obtain a homogeneous solution. The obtained solution was filtered in a container cooled to 5° C., having 1 mg of the 1-propanol/cyclohexane/hydrate of (R)-(−)-N-(1,1,3-trimethylindan-4-yl)-1-methyl-3-difluoromethylpyrazole-4-carboxylic acid amide obtained in Reference Example 8, and the obtained suspension was stirred at 5° C. for 2 hours. The obtained mixture was filtered and the obtained solid was dried in air for 1 hour to obtain a solid of the 1-propanol/cyclohexane/hydrate of (R)-(−)-N-(1,1,3-trimethylindan-4-yl)-1-methyl-3-difluoromethylpyrazole-4-carboxylic acid amide. The XRD chart, the FT-Raman spectrum, and the DSC/TGA chart of the obtained solid are shown in FIG. 17, FIG. 18, and FIG. 19, respectively.

Reference Example 10

To 100 mg of the (R)-(−)-N-(1,1,3-trimethylindan-4-yl)-1-methyl-3-difluoromethylpyrazole-4-carboxylic acid amide synthesized in Reference Example 1 was added 750 μL of tetrahydrofuran/water (volume ratio: 20/80). The obtained suspension was stirred for 40 hours while repeating warming and cooling within a range from 30° C. to 5° C. The obtained suspension was filtered and the obtained filtrate was cooled to 4° C. for 5 days and cooled to −20° C. for 24 hours. The obtained mixture was filtered and the obtained solid was dried in air for 1 hour to obtain a solid of the tetrahydrofuran/hydrate of (R)-(−)-N-(1,1,3-trimethylindan-4-yl)-1-methyl-3-difluoromethylpyrazole-4-carboxylic acid amide. The XRD chart of the obtained solid is the same as in FIG. 20.

Reference Example 11

To 301 mg of the (R)-(−)-N-(1,1,3-trimethylindan-4-yl)-1-methyl-3-difluoromethylpyrazole-4-carboxylic acid amide synthesized in Reference Example 1 was added 1.6 mL of tetrahydrofuran/water (volume ratio: 20/80). The obtained suspension was stirred at 30° C. for 1 hour. The obtained suspension was cooled to 5° C. To the obtained mixture was added 2 mg of the tetrahydrofuran/hydrate of (R)-(−)-N-(1,1,3-trimethylindan-4-yl)-1-methyl-3-difluoromethylpyrazole-4-carboxylic acid amide obtained in Reference Example 10, followed by stirring for 20 hours. The obtained mixture was filtered and the obtained solid was dried in air for 1 hour to obtain a solid of the tetrahydrofuran/hydrate of (R)-(−)-N-(1,1,3-trimethylindan-4-yl)-1-methyl-3-difluoromethylpyrazole-4-carboxylic acid amide. The XRD chart, the FT-Raman spectrum, and the DSC/TGA chart of the obtained solid are shown in FIG. 20, FIG. 21, and FIG. 22, respectively.

Reference Example 12

To 100 mg of the (R)-(−)-N-(1,1,3-trimethylindan-4-yl)-1-methyl-3-difluoromethylpyrazole-4-carboxylic acid amide synthesized in Reference Example 1 were added 750 μL of heptane and 30 μL of dimethylsulfoxide. The obtained suspension was stirred for 40 hours while repeating warming and cooling within a range from 30° C. to 5° C. The obtained mixture was filtered and the obtained solid was dried in air for 1 hour to obtain a solid of dimethylsulfoxide solvate of (R)-(−)-N-(1,1,3-trimethylindan-4-yl)-1-methyl-3-difluoromethylpyrazole-4-carboxylic acid amide. The XRD chart of the obtained solid is the same as in FIG. 23.

Reference Example 13

To 301 mg of the (R)-(−)-N-(1,1,3-trimethylindan-4-yl)-1-methyl-3-difluoromethylpyrazole-4-carboxylic acid amide synthesized in Reference Example 1 were added 2.2 mL of heptane and 90 μL of dimethylsulfoxide. The obtained suspension was stirred at 30° C. for 1 hour. The obtained suspension was cooled to 5° C. To the obtained mixture was added 2 mg of dimethylsulfoxide solvate of (R)-(−)-N-(1,1,3-trimethylindan-4-yl)-1-methyl-3-difluoromethylpyrazole-4-carboxylic acid amide obtained in Reference Example 12, followed by stirring for 20 hours. The obtained mixture was filtered and the obtained solid was dried in air for 15 minutes. To the obtained solid was added 2.0 mL of heptane, followed by stirring at room temperature for 4 hours. The obtained mixture was filtered and the obtained solid was washed with 3.0 mL of heptane. The obtained solid was dried at 50° C. for 20 hours while bubbling with nitrogen under reduced pressure to obtain a solid of the dimethylsulfoxide solvate of (R)-(−)-N-(1,1,3-trimethylindan-4-yl)-1-methyl-3-difluoromethylpyrazole-4-carboxylic acid amide. The XRD chart, the FT-Raman spectrum, and the DSC/TGA chart of the obtained solid are shown in FIG. 23, FIG. 24, and FIG. 25, respectively.

Reference Example 14

To 5.1 g of (R)-(−)-N-(1,1,3-trimethylindan-4-yl)-1-methyl-3-difluoromethylpyrazole-4-carboxylic acid amide synthesized in Example 3 was added 6.5 g of xylene. The obtained suspension was stirred at 75° C. for 1 hour to obtain a homogeneous solution. The obtained solution was cooled to 40° C. and stirred for 22 hours. The obtained mixture was filtered and the obtained solid was washed with 4.7 g of xylene. The obtained solid was dried at 50° C. for 3 hours under reduced pressure to obtain a solid of the xylene solvate of (R)-(−)-N-(1,1,3-trimethylindan-4-yl)-1-methyl-3-difluoromethylpyrazole-4-carboxylic acid amide. The XRD chart and the TG/DTA chart of the obtained solid are shown in FIG. 26 and FIG. 27, respectively.

INDUSTRIAL APPLICABILITY

According to the present invention, (R)-1,1,3-trimethyl-4-aminoindane can be obtained in a high yield.

The invention claimed is:

1. A method for producing (R)-1,1,3-trimethyl-4-aminoindane, comprising the following steps (A), (B), and (C):
   (A): a step of optically resolving 1,1,3-trimethyl-4-aminoindane to obtain (R)-1,1,3-trimethyl-4-aminoindane and (S)-1,1,3-trimethyl-4-aminoindane;
   (B): a step of racemizing the (S)-1,1,3-trimethyl-4-aminoindane obtained in the step (A) or (C) to obtain 1,1,3-trimethyl-4-aminoindane; and
   (C): a step of optically resolving the 1,1,3-trimethyl-4-aminoindane obtained in the step (B) to obtain (R)-1,1,3-trimethyl-4-aminoindane and (S)-1,1,3-trimethyl-4-aminoindane.

2. The production method according to claim 1, wherein the steps (B) and (C) are repeated.

3. The production method according to claim 1, wherein the step (C) is a step of optically resolving the 1,1,3-trimethyl-4-aminoindane obtained in the step (B) and the 1,1,3-trimethyl-4-aminoindane obtained in a step other than the step (B) to obtain (R)-1,1,3-trimethyl-4-aminoindane.

4. The production method according to claim 1, comprising the following steps (A), (B'), (D), and (E):
   (A): a step of optically resolving 1,1,3-trimethyl-4-aminoindane to obtain (R)-1,1,3-trimethyl-4-aminoindane and (S)-1,1,3-trimethyl-4-aminoindane;
   (B'): a step of racemizing the (S)-1,1,3-trimethyl-4-aminoindane obtained in the step (A) or (E) to obtain 1,1,3-trimethyl-4-aminoindane;
   (D): a step of purifying the 1,1,3-trimethyl-4-aminoindane obtained in the step (B'); and
   (E): a step of optically resolving the 1,1,3-trimethyl-4-aminoindane obtained in the step (D) to obtain (R)-1,1,3-trimethyl-4-aminoindane and (S)-1,1,3-trimethyl-4-aminoindane.

5. The production method according to claim 4, wherein the steps (B'), (D), and (E) are repeated.

6. The production method according to claim 1, wherein the step (B) or (B') is a step of bringing the (S)-1,1,3-trimethyl-4-aminoindane obtained in the step (A) into contact with a transition metal catalyst to perform racemization.

7. The production method according to claim 1, wherein the step (A) is a step comprising the following steps (A1), (A2), (A3), and (A4):
   (A1): a step of mixing 1,1,3-trimethyl-4-aminoindane with D-tartaric acid and methanol to obtain a mixture including a methanol solvate of D-tartrate of (R)-1,1,3-trimethyl-4-aminoindane and D-tartrate of (S)-1,1,3-trimethyl-4-aminoindane;
   (A2): a step of separating a solution containing D-tartrate of (S)-1,1,3-trimethyl-4-aminoindane and the methanol solvate of D-tartrate of (R)-1,1,3-trimethyl-4-aminoindane from the mixture obtained in the step (A1);
   (A3): a step of mixing the methanol solvate of D-tartrate of (R)-1,1,3-trimethyl-4-aminoindane obtained in the step (A2) and an aqueous alkali metal hydroxide solution or aqueous alkali metal carbonate solution to obtain (R)-1,1,3-trimethyl-4-aminoindane; and
   (A4): a step of mixing the solution including the D-tartrate of (S)-1,1,3-trimethyl-4-aminoindan obtained in the step (A2) and an aqueous alkali metal hydroxide solution or aqueous alkali metal carbonate solution to obtain (S)-1,1,3-trimethyl-4-aminoindane.

8. The production method according to claim 7, wherein water is mixed into the reaction system prior to the step (A2).

9. The production method according to claim 4, wherein the step (D) is a step comprising the following steps (D1), (D2), (D3), and (D4):
   (D1): a step of reacting the 1,1,3-trimethyl-4-aminoindane obtained in the step (B') with hydrogen hydride in the presence of water and a water-insoluble organic solvent;
   (D2): a step of separating a layer dissolving therein a hydrogen halide salt of 1,1,3-trimethyl-4-aminoindane included in the mixture obtained in the step (D1) from other layer;
   (D3): a step of precipitating the hydrogen halide salt of 1,1,3-trimethyl-4-aminoindane from the layer dissolving therein the hydrogen halide salt of 1,1,3-trimethyl-4-aminoindane obtained in the step (D2); and
   (D4): a step of withdrawing the hydrogen halide salt of 1,1,3-trimethyl-4-aminoindane obtained in the step (D3) and reacting thus obtained hydrogen halide salt with a base.

10. The production method according to claim 9, wherein the hydrogen halide is hydrogen chloride.

11. A method for producing a compound represented by the following formula (1):

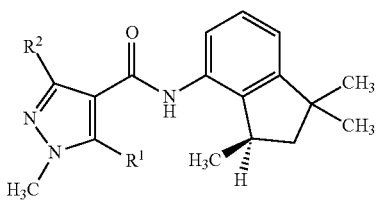

(1)

wherein $R^1$ and $R^2$ each independently represent an alkyl group which may be substituted with a halogen atom, or a hydrogen atom), comprising the following steps (A), (B), (C), and (F):

(A): a step of optically resolving 1,1,3-trimethyl-4-aminoindane to obtain (R)-1,1,3-trimethyl-4-aminoindane and (S)-1,1,3-trimethyl-4-aminoindane;

(B): a step of racemizing the (S)-1,1,3-trimethyl-4-aminoindane obtained in the step (A) or (C) to obtain 1,1,3-trimethyl-4-aminoindane;

(C): a step of optically resolving the 1,1,3-trimethyl-4-aminoindane obtained in the step (B) to obtain (R)-1,1,3-trimethyl-4-aminoindane and (S)-1,1,3-trimethyl-4-aminoindane; and (F): a step of reacting the (R)-1,1,3-trimethyl-4-aminoindane obtained in the step (C) with a compound represented by the formula (2) to obtain a compound represented by the formula (1):

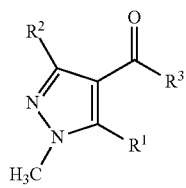

(2)

wherein $R^1$ and $R^2$ represent the same meanings as above, and $R^3$ represents a halogen atom, a hydroxyl group, or an alkoxy group which may be substituted with a halogen atom.

12. A method for producing a compound represented by the following formula (1):

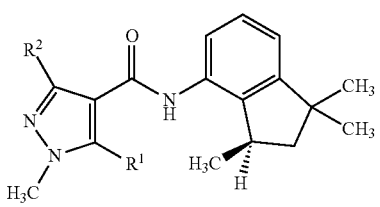

(1)

wherein $R^1$ and $R^2$ each independently represent an alkyl group which may be substituted with a halogen atom, or a hydrogen atom), comprising the following steps (A), (B), (C), (G), and (H):

(A): a step of optically resolving 1,1,3-trimethyl-4-aminoindane to obtain (R)-1,1,3-trimethyl-4-aminoindane and (S)-1,1,3-trimethyl-4-aminoindane;

(B): a step of racemizing the (S)-1,1,3-trimethyl-4-aminoindane obtained in the step (A) or (C) to obtain 1,1,3-trimethyl-4-aminoindane;

(C): a step of optically resolving the 1,1,3-trimethyl-4-aminoindane obtained in the step (B) to obtain (R)-1,1,3-trimethyl-4-aminoindane and (S)-1,1,3-trimethyl-4-aminoindane;

(G): a step of obtaining a compound represented by the formula (4) from a compound represented by the formula (3):

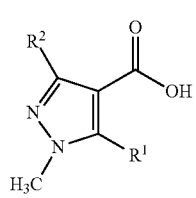

(3)

wherein $R^1$ and $R^2$ represent the same meanings as above

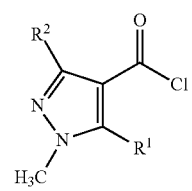

(4)

wherein $R^1$ and $R^2$ represent the same meanings as above; and (H): a step of reacting the compound represented by the formula (4) obtained in the step (G) with the (R)-1,1,3-trimethyl-4-aminoindane obtained in the step (C) in the presence of a base to obtain the compound represented by the formula (1).

13. The production method according to claim 11, wherein $R^1$ is a hydrogen atom or a methyl group, and $R^2$ is a methyl group, a monofluoromethyl group, a difluoromethyl group, or a trifluoromethyl group.

* * * * *